(12) United States Patent
Haindl et al.

(10) Patent No.: US 8,827,955 B2
(45) Date of Patent: Sep. 9, 2014

(54) CANNULA DEVICE HAVING PIVOTABLE NEEDLE GUARD

(75) Inventors: Hans Haindl, Wennigsen (DE);
Reinhard Kruse, Gelnhausen (DE);
Michael Kaufmann, Wachtersbach (DE)

(73) Assignee: Suddeutsche Feinmechanik GmbH, Wachtersbach (DE)

( * ) Notice: Subject to any disclaimer, the term of this patent is extended or adjusted under 35 U.S.C. 154(b) by 295 days.

(21) Appl. No.: 12/671,243

(22) PCT Filed: Jul. 31, 2008

(86) PCT No.: PCT/EP2008/060065
§ 371 (c)(1),
(2), (4) Date: Jan. 29, 2010

(87) PCT Pub. No.: WO2009/016234
PCT Pub. Date: Feb. 5, 2009

(65) Prior Publication Data
US 2010/0198152 A1 Aug. 5, 2010

(30) Foreign Application Priority Data

Aug. 1, 2007 (DE) .......................... 10 2007 036 507
Mar. 6, 2008 (DE) .......................... 10 2008 002 796
May 21, 2008 (DE) .......................... 10 2008 002 858

(51) Int. Cl.
*A61M 5/00* (2006.01)
*A61M 5/50* (2006.01)
*A61M 5/32* (2006.01)

(52) U.S. Cl.
CPC ........... *A61M 5/3216* (2013.01); *A61M 5/5086* (2013.01); *A61M 2005/3247* (2013.01)
USPC ......................................... 604/110

(58) Field of Classification Search
CPC ...................................... A61M 5/3216
USPC .................................. 604/110, 263
See application file for complete search history.

(56) References Cited

U.S. PATENT DOCUMENTS

| 3,658,061 A | 4/1972 | Hall |
| 4,664,259 A | 5/1987 | Landis |
| 5,135,509 A | 8/1992 | Olliffe |

(Continued)

FOREIGN PATENT DOCUMENTS

| DE | 8705966 | 6/1987 |
| EP | 0819441 | 1/1998 |
| WO | 9316745 | 9/1993 |

*Primary Examiner* — Aarti B Berdichevsky
(74) *Attorney, Agent, or Firm* — Ladas & Parry LLP

(57) ABSTRACT

A cannula device having a base body made of plastic, on which a cannula is held, and having a guard element that can be moved relative to the base body into a second position, in which the cannula tip is exposed for the use of the cannula device, from a first position, in which, in the delivered state of the cannula device, the cannula tip is covered to protect the user from injury. The guard element is movable, after use of the cannula device, back into a third position in which the cannula tip is covered to protect a user from injury, and the guard element is irreversibly locked to the base body by a third fixing device including a first latching protrusion protruding from the base body and at least one first latching receptacle, associated with the first latching protrusion in at least one side wall of the guard element.

53 Claims, 19 Drawing Sheets

(56) References Cited

U.S. PATENT DOCUMENTS

| | | |
|---|---|---|
| 5,207,653 A | 5/1993 | Janjua et al. |
| 5,405,332 A * | 4/1995 | Opalek .................. 604/192 |
| 5,490,841 A | 2/1996 | Landis |
| 5,632,732 A | 5/1997 | Szabo et al. |
| 5,649,622 A * | 7/1997 | Hollister ................. 206/365 |
| 5,807,351 A | 9/1998 | Kashner |
| 5,868,716 A | 2/1999 | Sweeney et al. |
| 6,599,268 B1 | 7/2003 | Townsend et al. |
| 6,645,182 B1 | 11/2003 | Szabo |
| 6,811,547 B2 | 11/2004 | Wilkinson |
| 2003/0028150 A1 * | 2/2003 | Tuen ....................... 604/197 |
| 2003/0036732 A1 * | 2/2003 | Marano-Ford ........... 604/199 |
| 2006/0149188 A1 | 7/2006 | Simas |

\* cited by examiner

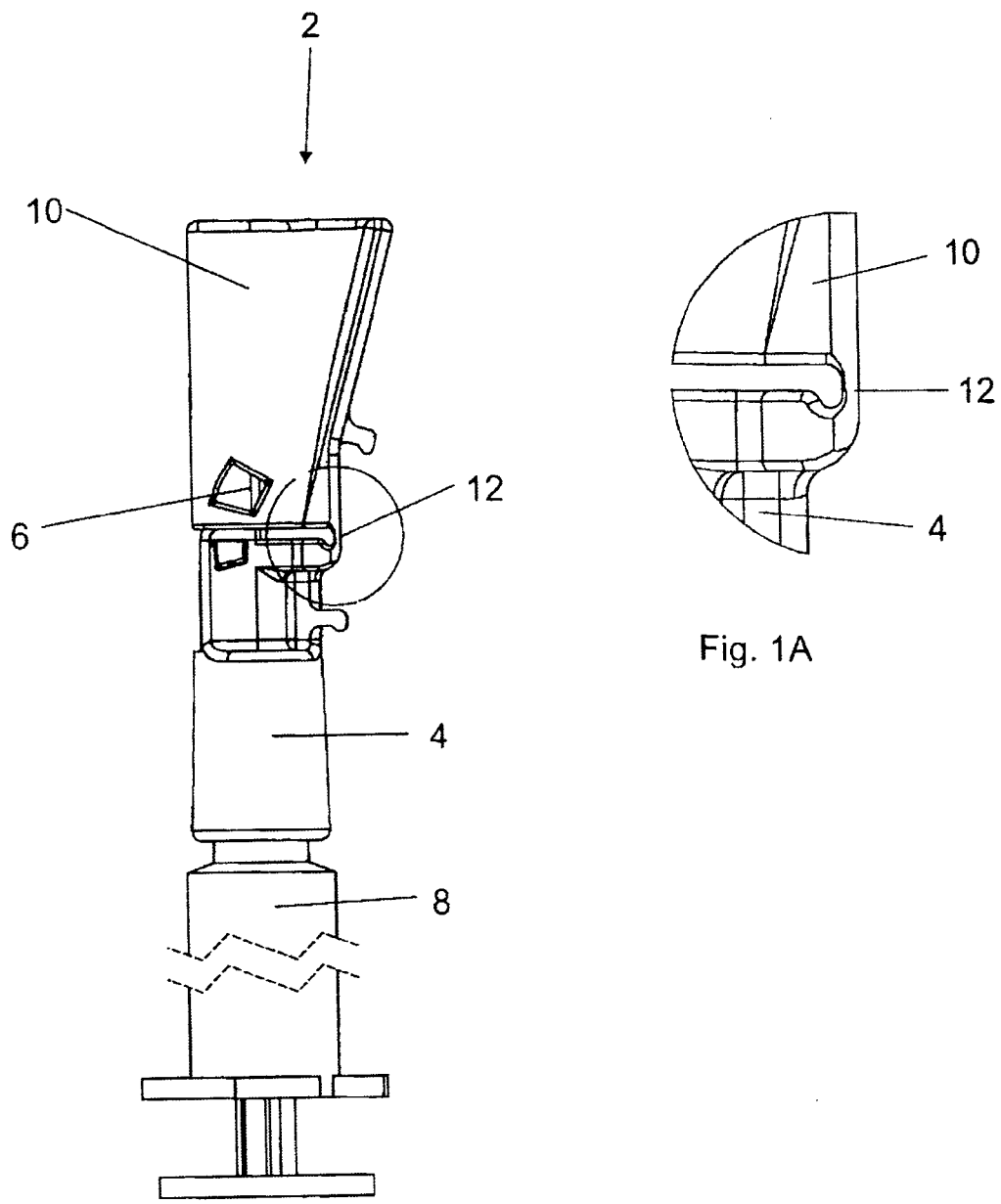

CANNULA DEVICE HAVING PIVOTABLE NEEDLE GUARD

The invention relates to a cannula device having a base body made of plastic, on which a cannula having a cannula tip is held, and having a safety element, which is preferably designed in one piece with the base body and in particular is connected to the latter by a hinge-type mechanism and can be moved out of a first position, in which the cannula tip is covered to protect the user from injury in the as-delivered state of the cannula device, into a second position, in which the cannula tip is exposed for use of the cannula device, wherein the safety element can be moved back into the first position or into a third position, in which the cannula tip is covered to protect the user from injury after the cannula device has been used, and the safety element is irreversibly locked to the base body by third fixation means.

Such cannula devices are known in general as so-called safety cannulas and are used to inject fluids into and/or to withdraw them from the human or animal body.

Cannula devices in which the cannula can be covered by a separate safety element, also known as a safety body or safety cap, are described, for example, in US 2006/0100576 A, GB 2,277,685 A (U.S. Pat. No. 5,423,765 A), WO 2006/041 442 A, WO 2005/030 290 A, WO 2006/074121 A (US 2006/0149188 A) or US 2006/0129126 A.

WO 90/01348 A discloses a generic cannula device, consisting of a base body made of plastic surrounding a cannula and a safety cap, which is designed as an integral component thereof and is pivotable. The safety cap may be irreversibly locked to the base body in a third position after use of the cannula. Therefore, one or more fingers lead away from the inside of the safety cap and engage in recesses in the base body. To prevent the safety cap from swinging back in the other direction in an uncontrolled manner, the recesses must be relatively deep and thus the base body must have an undesirably thick wall thickness. This in turn results in a very bulky safety cap in the area of the base body.

Additional proposals, according to which a cannula can be covered after use by means of a safety cap pivotable toward a base body, are known from such documents as U.S. Pat. No. 5,632,732 A, U.S. Pat. No. 5,207,653 A, DE-U-87 05 966, U.S. Pat. No. 3,658,061 A and U.S. Pat. No. 4,664,259 A. The base body and safety cap here are elements which are manufactured separately and then assembled.

EP 1 384 439 A and U.S. Pat. No. 5,490,841 A provide a safety cap designed as an integral component with a base body surrounding a cannula, so that the cannula can be covered by the safety cap. After use of the cannula, the safety cap can surround the cannula, so that uncontrolled pivoting of the safety cap is no longer possible.

According to WO 90/03195 A, U.S. Pat. No. 4,702,738 A or U.S. Pat. No. 4,935,012 A, a safety cap is displaced in the longitudinal direction of a cannula, resulting in a complete removal of the cannula for use. Next the safety caps are attached again. One disadvantage of this design is that the safety cap is removed and set aside during use, so that reattachment is often impossible.

A safety cap and/or safety body connected to the base body surrounding the cannula is/are disclosed in U.S. Pat. No. 5,807,351 A. The disadvantage of this design is that the cannula is locked in the same position with the base body in the as-delivered state, i.e., before use, as it is after use, so that consequently the safety cap can also be removed easily from a cannula that has been used.

The object of the present invention is to improve upon a cannula device of the type defined in the introduction, so that there is the possibility of problem-free use and protection for the user after use of the cannula, and this is accomplished with simple means, in particular so that it is impossible to unintentionally remove the safety body, which is also known as a safety cap, from the cannula after use of the cannula. According to another object of the invention, it should be ensured that the safety body cannot be pivoted in an uncontrolled manner while the cannula is being used. According to one aspect of the invention, it should also be possible to ascertain easily whether the cannula is as yet unused.

This object is essentially achieved according to the present invention by the fact that the third fixation means comprise at least one first catch projection protruding away from the base body and at least one first catch recess in at least one side wall of the safety element, said recess being allocated to the catch projection.

Inventive embodiments and further refinements are derived from the claims.

The as-delivered state of the cannula device is understood according to the present invention to refer to the state of the cannula device after its production and before its use, e.g., before performing a puncture, and in which the cannula device has been packaged in a sterile manner in particular. According to the invention, the safety element in this as-delivered state is in the first position, in which the tip of the cannula is covered to protect the user from injury. To bring the cannula device into a use state, in which a puncture can be performed, for example, the user moves the safety element into the second position, in which the cannula tip is exposed. After use of the cannula device, the user brings the safety element into a third position, in which the cannula tip is covered to protect the user from injury. In this way, the user of the inventive cannula device is reliably protected from needle puncture injuries in the as-delivered state of the cannula device as well as after its use. In the third position, the safety cap locks irreversibly onto the base body. To do so, it is provided according to the present invention that the third fixation means comprise at least one first catch projection protruding away from the base body and at least one first catch recess allocated to said catch projection in at least one side wall of the safety element. Due to the fact that at least one catch projection leads away from the base body and engages in a catch recess, in particular in an opening in the base body, the base body may have a compact shape without having to accept any sacrifices with regard to the locking engagement and thus the safety of the user. In particular when the catch projection engages in the catch recess like a hook, in particular in an opening, this permits a secure and thus irreversible locking engagement, assuming the usual handling.

To further increase the safety from puncture injuries and to make it possible to check on whether the cannula has been used and/or was previously uncovered, according to one proposal of the present invention, the safety element in the as-delivered state is connected to the base body by an tamper-proof seal and/or the safety element is affixed in the first position by first fixation means before the use of the cannula device. This reduces the risk that a user might inadvertently move the safety element into the second position and thereby suffer a needle puncture injury due to the cannula tip, which is thereby exposed.

If the safety element, also referred to as a safety body or safety cap, is connected to the base body by a tamper-proof closure in the as-delivered state, then this must be destroyed when the cannula is exposed, i.e., the safety body must be pivoted toward the cannula. In other words, the tamper-proof closure more or less forms a seal of the safety body with the base body holding the cannula and is necessarily destroyed when the safety body has been pivoted toward the cannula.

In particular it is provided that to form the tamper-proof closure, the safety cap is bonded to the base body, in particular by heat bonding. Alternatively, the safety cap may be ultrasonically spot-welded to the base body to form the tamper-proof closure. According to another alternative approach, to form the tamper-proof closure, the safety cap is attached to the base body by a strip of adhesive tape, such as a label.

The safety cap or at least one of its side walls may also be attached to the base body by a type of film or thin membrane, which is formed in injection molding and must be destroyed when the cannula is exposed, i.e., when the safety cap is to be pivoted. The film and/or membrane may be present in addition to or as an alternative to the embodiments of the tamper-proof closure described above.

Regardless of the embodiment of the tamper-proof closure, it should run at a distance from at least one articulation point, by means of which the safety body is connected to the base body.

Furthermore, in addition to the tamper-proof closure, the safety element and/or safety body may be locked onto the base body in the first position, i.e., in the as-delivered state.

To implement the third fixation means, two first catch projections running symmetrically with a plane lead away from the base body, a first catch recess in one of the side walls being allocated to each catch projection. The cannula runs in the plane itself.

To achieve a simple structural design and to be able to produce the cannula safety device by injection molding using inexpensive tools, the two first catch projections protrude away from a web-shaped section of the base body extending along the cannula itself, preferably with the cannula passing through it. The catch projections should develop one into the other and on the average should have a trapezoidal geometry with a larger base leg running proximally. This permits simple locking engagement in the first catch recess.

The dimensions of the catch projection and the wall thickness of the side wall should preferably be coordinated with one another, so that when the catch projection is locked in the catch recess, it runs completely inside the first catch recess like an opening, with the free outer edge area of the recess running across the longitudinal axis of the cannula body.

In particular, the web-shaped section from which the catch projections extend is the longitudinal leg of a distal section of the base body having a T-shaped geometry, such that the cannula can pass through the longitudinal leg. On one side of the cannula, the transverse leg of the T-shaped section forms the catch projections. On the opposite side of the cannula, sections protrude laterally away from the web-shaped longitudinal leg from the opposite side of the cannula, and the cannula body is connected to the safety body by film hinges by means of these sections.

In particular the cannula passes through the base body and is glued in place there or is sheathed by it on injection. However, there is also the possibility of bonding as well as locking engagement of the base body to a cannula attachment. Regardless of this, the base body should develop proximally into a section that is preferably designed as a Luer cone and/or as a Luer connecting body to enable a connection, e.g., to a syringe body or a tube connection.

Protection against inadvertent detachment when the safety cap is in the third position can be achieved in particular by the fact that the fixation by the fixation means cannot be released by hand but instead can be released only by using a tool. For example and in particular, the safety element may be locked to the base body in the third position in such a manner that cannot be overcome without using a tool.

To further ensure that after use of the cannula and its cover by the safety body, the cannula cannot be used again, e.g., when the safety body is pivoted away from the cannula by targeted intervention into the locking engagement in the third position, which is accomplished between the base body and the safety body, it is provided that when the cannula is in the third position of the safety body, it is bent by the latter.

According to the respective requirements, the safety element may execute any suitable movement between the first position and the second position. According to an advantageous further embodiment of the inventive teaching, the safety element is pivotably connected to the base body. In this way, the design of the inventive cannula device is further simplified because a pivoting connection between the safety element and the base body can be implemented in an especially simple manner, in particular in injection molding of the safety element and the base body from plastic.

According to another advantageous further refinement of the inventive teaching, the safety element is connected to the base body like a hinge, in particular by means of at least one film hinge. In particular film hinges can be manufactured especially easily by an injection molding method in manufacturing the safety element in one piece with the base body.

With regard to the inventive feature of the tamper-proof closure, it is provided in the further embodiment that the safety body is bonded to the distal section, in particular to the transverse leg of the distal section of the base body, or is spot-welded to it, e.g., by ultrasonic spot welding.

Each side wall of the safety body is preferably bonded or spot-welded, in particular by ultrasonic welding, to the proximal catch projection outside of the catch recess. To be able to easily manufacture and test the tamper-proof closure, the connection between the safety body and the base body forming the tamper-proof closure should be provided in the area of the end faces of the side walls and the transverse leg.

If a tamper-proof closure is implemented by at least one strip of adhesive tape, such as a label, then it should run along at least one exterior surface of one of the side walls of the safety body and should lead to the base body. To be sure that the strip of adhesive tape cannot be pulled away nondestructively, corresponding perforations are provided. Regardless of this, a perforation should run between the base body and the safety body, so that the strip of adhesive tape and/or the label does not interfere with intentional pivoting of the safety body. In particular a strip of adhesive tape and/or a label, which leads to the base body, extends away from each side wall.

The fixation means may essentially be detachable fixation means. For example, the first fixation means may have catch means, by which the safety element is locked in the first position with the base body of the cannula device, such that the catch connection can be released by hand to prepare the cannula device for use. To prevent unwanted release of the catch connection, the catch means may be covered, e.g., by a strip of adhesive tape or the like. To reduce the resulting manufacturing complexity due to the fact that detachable fixation means for fixation of the safety element in the first position are omitted, according to an advantageous further embodiment of the inventive teaching, the first fixation means have at least one fixation element that can be detached when the safety element is moved out of the first position and into the second position. In this embodiment, the safety element is first affixed in the first position via the fixation element on the base body. After detaching and thus destroying the fixation element, the safety element may then be moved into the second position, in which the tip of the needle is exposed.

The shape and size of the fixation element can be selected within additional limits in accordance with the respective requirements. The same thing is also true of the number of fixation elements, if more than one fixation element is present. According to an advantageous further embodiment of the inventive approach, the fixation element is designed like a film. In this way, the fixation element can be manufactured especially easily and using only a minor amount of material. Through an appropriate choice of the thickness of the film, it is possible to ensure that the safety element is adequately secured on the base body in the first position, but on the other hand, the fixation element is reliably detached when the safety element is moved into the second position.

To simplify movement of the safety element into the second position, according to another advantageous further embodiment of these designs with the fixation element, the latter has at least one weakened spot in the materials, thereby facilitating the detachment of the fixation element when the safety element is moved out of the first position and into the second position.

The fixation element may be designed according to the invention as a separate component, which is manufactured separately from the base body and the safety element and is connected to the safety element and the base body by suitable connecting means. According to the invention, the fixation element may in particular also be designed in one piece with both the base body and the safety element. According to a further advantageous embodiment of the inventive teaching, the fixation element is designed at its one end in one piece with the base body and/or the safety element and is connected at its other end to the safety element and/or the base body by the connecting means. In this embodiment, the fixation element is designed in one piece with one of the components, whereas it is connected by connecting means to the other component. This embodiment has the advantage in particular that a unit comprising the base body, the safety element and the fixation element can be manufactured in one piece and opened, and the cannula may be glued into the base body. After gluing the cannula into the base body, the unit may then be closed, whereupon the fixation element can be connected by connecting means to the component with which it is not designed in one piece.

To make the connection of the fixation element to the base body especially simple in the aforementioned embodiment, the connecting means have catch means in particular according to a further embodiment.

It is essentially sufficient according to the invention if the safety element sits loosely in the second position. However, according to an advantageous further embodiment of the inventive teaching, the safety element can be affixed in the second position by the second fixation means. In this embodiment, the safety element is prevented from moving out of the second position and into the first position in an unwanted manner, which would thus interfere with the use of the cannula device in an injection, for example. The second fixation means here may be detachable fixation means in particular, so that after the cannula device has been used, the safety element can be moved back into the first position or into another position, in which the tip of the cannula is covered to protect the user from injury.

According to a further refinement of the aforementioned embodiment, the safety element is connected to the base body by a dead center arrangement, which has a dead center in the second position of the safety element. In this embodiment, the safety element is held in a stable manner in the second position for use of the cannula device, but by overcoming the dead center, it can easily be moved by the user back into the first position or another position, in which the tip of the cannula is covered to protect the user from injury.

According to an advantageous further embodiment of a combination of the aforementioned embodiment with the embodiment in which the safety element is connected like a hinge to the base body, the dead center arrangement is formed by the hinge-type connection, in particular the film hinge. In this embodiment, no additional means, such as catch means, are required in addition to the hinge-type connection, which is present anyway, to hold the safety element in the second position in a stable manner. In the case of a film hinge, a dead center arrangement may be formed in particular by the fact that the film hinge has two or more individual hinges, which are arranged in different planes.

To allow problem-free pivoting of the safety body with guidance thereof at the same time, the safety body should preferably be hinge-connected to the base body by film hinges at two articulation points and/or areas that are spaced a distance apart, connected.

In a further embodiment to be emphasized, a retaining hinge connecting the base body to the safety body with the dead center position in the use position as the second position should then run between the two hinge connection points and/or areas, which are spaced a distance apart. The retaining hinge is consequently designed in the manner of a snap hinge, such that when the safety body is pivoted toward the cannula to a certain extent, the retaining hinge automatically pivots the safety cap into an end position, which corresponds to a dead center position of the hinge. This ensures that in the use position, i.e., the second position, unintentional pivoting of the safety body is prevented, thereby allowing undisturbed handling of the cannula.

To simplify the manufacturing of the cannula device with the aforementioned embodiments, according to another embodiment of the inventive teaching, the second fixation means and/or the third fixation means are designed in one piece with the safety element and/or the base body. The base body together with the safety element is expediently designed as an injection-molded part made of plastic, as provided according to a further refinement of the inventive teaching.

Furthermore, the locking engagement should be such that it is positioned between the first and third positions, so that the inside of the rear wall of the safety body is closer to the cannula in the third position of the safety cap than in the first position.

According to one proposal, in order to enable a locking engagement in addition to the tamper-proof closure in the as-delivered state (first position), if necessary, it is provided that at least one second catch projection, which is paired with a second catch recess running in the side wall of the safety body, should protrude away from the longitudinal leg of the distal section of the base body having the T shape in the area of the cannula, said second catch recess being situated closer to the transverse edge of the side wall running toward the base body than the first catch recess.

In addition, the second catch projection protrudes away from the base body, in particular away from the longitudinal section of a T-shaped distal section in an area that is closer to the pivot axis than the first catch projection and/or is beneath the first catch projection, so that the arrangement of the first and second catch projections and the first and second catch recesses allocated to them ensures that the inside of the rear wall of the safety body is a greater distance away from the cannula in the first position (in the as-delivered state) than in the third position, i.e., in the position after the cannula has been used.

In particular, two second catch projections that run symmetrically with the longitudinal leg extend away from the longitudinal side leg of the distal section of the base body, such that a second catch recess in one of the side walls is allocated to each second catch projection.

In positioning the safety body in the third position, in order for the second catch projections not to result in them being in contact with the insides of the side walls and thus being able to press them outward, it is provided that a third catch recess runs in the side wall between the first and second catch recesses, the second catch projection protruding into this third catch recess when the safety body is in the third position.

The second catch projection has the geometry of a cylinder in particular, so that the second and/or third catch recesses have a circular geometry in the plane of the side wall, the cross section of the third catch recess in the plane of the side wall being larger than the cross section of the second catch recess. On the other hand, the first catch recess in the plane of the side wall has a rectangular geometry to receive the first catch projection, which has a rectangular geometry in the cross-sectional plane running parallel to the longitudinal leg of the distal section of the base body.

According to an alternative embodiment for locking engagement of the safety body in the first position, i.e., in the as-delivered state, a recess for a projection, which leads from the side wall of the safety body, pivotable along the side and connected to the side wall via a predetermined breaking point, proceeds away from at least one side of the longitudinal leg of the T-shaped distal section of the base body, said projection being affixed, e.g., locked, in the recess in the first position. This ensures a secure hold of the safety body in the first position, such that the projection is separated from the side wall due to the forces that occur in pivoting, so that consequently the safety body can be pivoted with no problem out of the first position and into the second position, i.e., into the position in which the cannula is to be used. The separation from the side wall is facilitated by a predetermined breaking point.

Thus, through the proposed approach in this regard, a tamper-proof closure with locking engagement at the same time is also provided.

In particular, a recess for a projection connected to the side wall via a predetermined breaking point leads away from each side of the longitudinal leg. It is provided here that the projection is connected to the side wall via a pivotable web-shaped section having the predetermined breaking point.

The projection may have a cylindrical shape with a reinforcement such as a torus provided on the free end, engaging beneath the recess with fixed positioning in the recess.

The recess may be bordered by two webs running parallel to one another and in particular also parallel to the longitudinal axis of the cannula and protruding away from the longitudinal leg of the T-shaped distal section of the base body. In the assembled position, i.e., before the safety body is pivoted into the first position to cover the cannula, the web-shaped section runs in the plane spanned by the side wall away from which the projection extends at a right angle. Consequently, to position the safety body in the first position, the projection is pivoted about the predetermined breaking point to engage in the recess, e.g., to lock there. In doing so, the reinforced end sits like a knob-like toroidal enlargement beneath the lower edges of the web-shaped sections bordering the recess.

To allow problem-free insertion of the projections having a cylindrical shape in particular, the webs forming the recess border a channel-shaped recess, which becomes wider conically at the end.

According to another embodiment for locking the safety body in the as-delivered state, i.e., in the first position, a two-armed leg pivotable toward the side wall leads away like a wing from the transverse edge area of the side wall on the side of the base body, said leg comprising a retaining section, which extends in the direction of the longitudinal leg of the T-shaped distal section of the base body, such that a second catch projection, which is offset toward the proximal section of the base body and at a distance from the first catch projection, extends away from the longitudinal leg, and the retaining section reaches beneath it in the first position of the safety body.

The pivotable wing-type leg is aligned toward the outside of the side wall, so that when no force is applied to the pivotable leg, it assumes a course diverging toward the side wall, starting from the hinge area. This allows the pivoting of the wing to be simplified. If the wing is adjusted in the direction of the side wall, then the retaining section, which runs beyond the connecting area with the side wall, becomes disengaged with the second catch projection accordingly, so that consequently the safety body can be pivoted.

Regardless of this, a pivotable leg such as a wing should lead away from each side wall and/or its transverse edge area, and a second catch projection should lead away from each side of the longitudinal leg of the T-shaped distal section of the base body, such that the second catch projections run symmetrically to the plane in which the longitudinal leg is situated.

To rule out the possibility that in the engaged third position (disposal state) of the safety body, the side walls might interact with sections of the first catch projections which might pass through the first catch recesses when the wings are pivoted in the direction of the side walls, possibly allowing the catch projections to unintentionally be forced out and then allowing pivoting of the safety body, it is proposed that the pivotable wing-type leg should have a recess such as an opening, which is aligned with the first catch recess, with a side wall in a nearby or contacting position of the wing.

The present invention is explained in greater detail below on the basis of the accompanying drawing, showing the exemplary embodiments of an inventive cannula device. All the features claimed in the patent claims, described in the text and illustrated in the drawings may constitute the subject matter of the present invention, either individually or in any combination with one another, regardless of how they are combined in the patent claims and in their reference back to other claims and regardless of their description and/or illustration in the drawings.

In the drawings:

FIG. 1 shows a side view of a first exemplary embodiment of an inventive cannula device, attached to a syringe, FIG. 1A shows a detail from FIG. 1 on an enlarged scale, FIG. 2 shows another side view of the cannula device according to FIG. 1, FIG. 2A shows a detail from FIG. 2 on an enlarged scale, FIG. 3 shows a view of the cannula device according to FIG. 1 as seen from above, FIG. 4 shows a partially sectional side view of the cannula device according to FIG. 1, FIG. 5 shows the cannula device according to FIG. 1 in the same type of diagram as in FIG. 1, with the safety element in the third position, FIG. 5A shows a detail from FIG. 5 on an enlarged scale, FIG. 6 shows the cannula device according to FIG. 5 during use in an injection, FIG. 7 shows the cannula device according to FIG. 1 in the same type of diagram as in FIG. 1, with the safety element in the third position, FIG. 7A shows a detail from FIG. 7 on an enlarged scale, FIG. 8 shows a view of the cannula device according to FIG. 7 as seen from above, FIG. 9 shows a partially sectional side view of the cannula device according to FIG. 7, FIG. 10 shows another embodiment of a cannula device and/or a cannula safety device, FIG. 11 shows the cannula safety device according to FIG. 10 with a first embodiment of a tamper-proof closure, FIG. 12 shows the cannula safety device according to FIG. 10 in the as-delivered state in a view from the rear, FIG. 13 shows the cannula safety device according to FIG. 10 in the disposal position (third position), FIG. 14 shows the shows the safety device according to FIG. 10 with a second embodiment of a tamper-proof closure, FIG. 15 shows a modification of the cannula safety device according to FIG. 10, FIG. 16 shows another embodiment of a cannula safety device in the assembled position, FIG. 17 shows the cannula safety device according to FIG. 16 in the as-delivered state (first position), FIG. 18 shows the cannula safety device according to FIG. 13 is the disposal position (third position), and FIG. 19 shows another embodiment of a cannula safety device.

FIG. 1 shows a first exemplary embodiment of an inventive cannula device 2 having a base body 4 made of plastic, on which a cannula 6 (only partially visible in FIG. 1) is held with the tip of the cannula (also not visible in FIG. 1). The base body 4 may be designed as a female Luer connector, for example, to facilitate connection to a syringe 8, as indicated schematically in FIG. 1. The cannula device 2 also has a safety element 10 (hereinafter also referred to as a safety body or safety cap), which is movable in relation to the base body 4 between a first position, shown in FIG. 1, where the tip of the cannula is covered to protect the user from injury, and a second position, which is explained in greater detail below and in which the tip of the cannula is exposed for use of the cannula device 2.

The safety element 10 is made of plastic and is designed in particular in one piece with the base body 4.

In this exemplary embodiment, the unit of the base body 4 and safety element 10 is embodied as an injection-molded part produced by an injection molding method. Furthermore, in this exemplary embodiment, the safety element 10 is pivotable about a pivot axis running into the plane of the drawing in FIG. 1, namely by means of a film hinge 12, and is connected like a hinge to the base body 4. Since the film hinge 12 connects the base body 4 to the safety element 10, it is also embodied in one piece with the base body 4 and the safety element 10. FIG. 1A shows a detail from FIG. 1 in the area of the film hinge 12.

FIG. 2 shows the cannula device 2 in another view, where the cannula 6 and its cannula tip 14 can be seen. FIG. 2 also shows that the safety element 10 is embodied so that it is open toward the user in FIG. 2. However, in other embodiments of an inventive cannula device 2, the safety element 10 may also be embodied as a cap.

In the as-delivered state (first position), the safety element 10 (hereinafter also referred to as the safety body or safety cap) is affixed to the base body 4. To do so, according to the exemplary embodiment of FIGS. 1 to 9, first fixation means are provided, having a fixation element 16, which is embodied in this exemplary embodiment as a thin film-like web joining the opposite free axial ends of the base body 4 and the safety element 10 to one another. The fixation element 16 extends into the plane of the drawing, i.e., essentially a short distance in the circumferential direction of the cannula 6. It has a weakening of the material, e.g., in the form of an indentation, such that it facilitates the detachment of the fixation element 16 when the safety element moves out of the position shown in FIG. 2 into a second position shown in FIG. 5 (useful position). In this exemplary embodiment, the fixation element 16 is embodied in one piece with the base body 4 and the safety element 10 at both of its axial ends, based on the cannula 6.

In the radial direction of the cannula 6 toward the fixation element 16, another fixation element 16' is provided, designed symmetrically to the fixation element 16 accordingly and therefore not explained further here.

The base body 4 may be embodied in one piece as an injection-molded part together with the safety element 10 and the fixation elements 16, 16', such that the fixation elements 16, 16' are integrally molded on the base body 4 and the safety element 10 during the injection molding.

Figures 2, 2A:
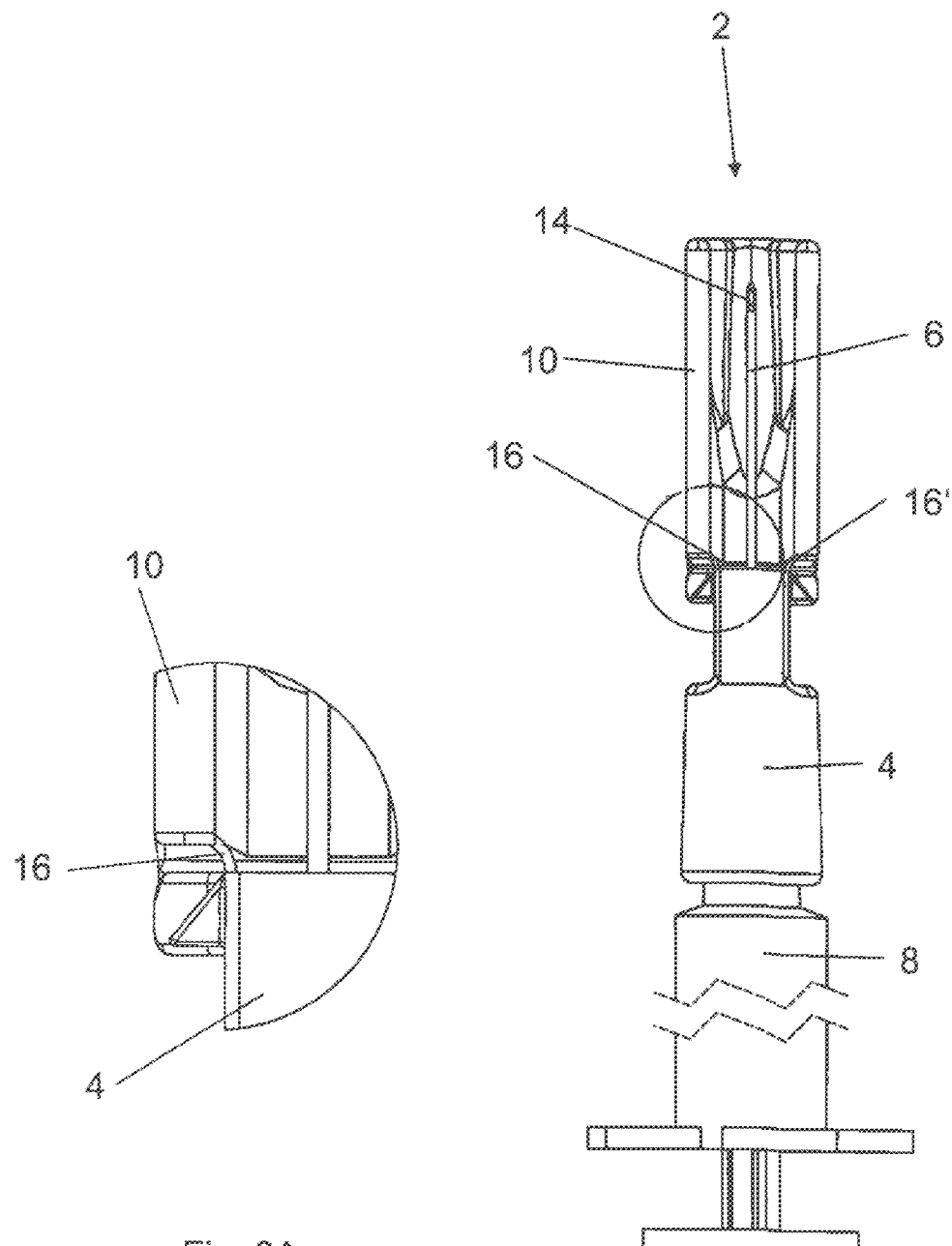
FIG. 2A shows an enlarged detail from FIG. 2, in which the fixation element 16 can be seen especially well.
Figure 3:
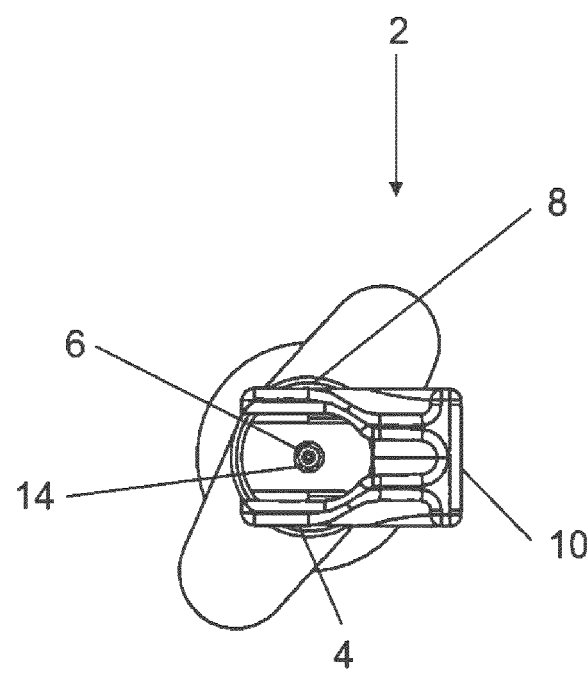
FIG. 3 shows a view of the cannula device 2 from above.

For fixation of the safety element 10 in the second position of the safety element 10, which is explained in greater detail further below with reference to FIG. 5, in relation to the base body 4, two fixation means are provided, having in this exemplary embodiment catch means, which have two hook-like catch projections 18, 20, of which the catch projection 18 is arranged on the safety element 10 and the catch projection 20 is arranged on the base body 4.

Figure 4:
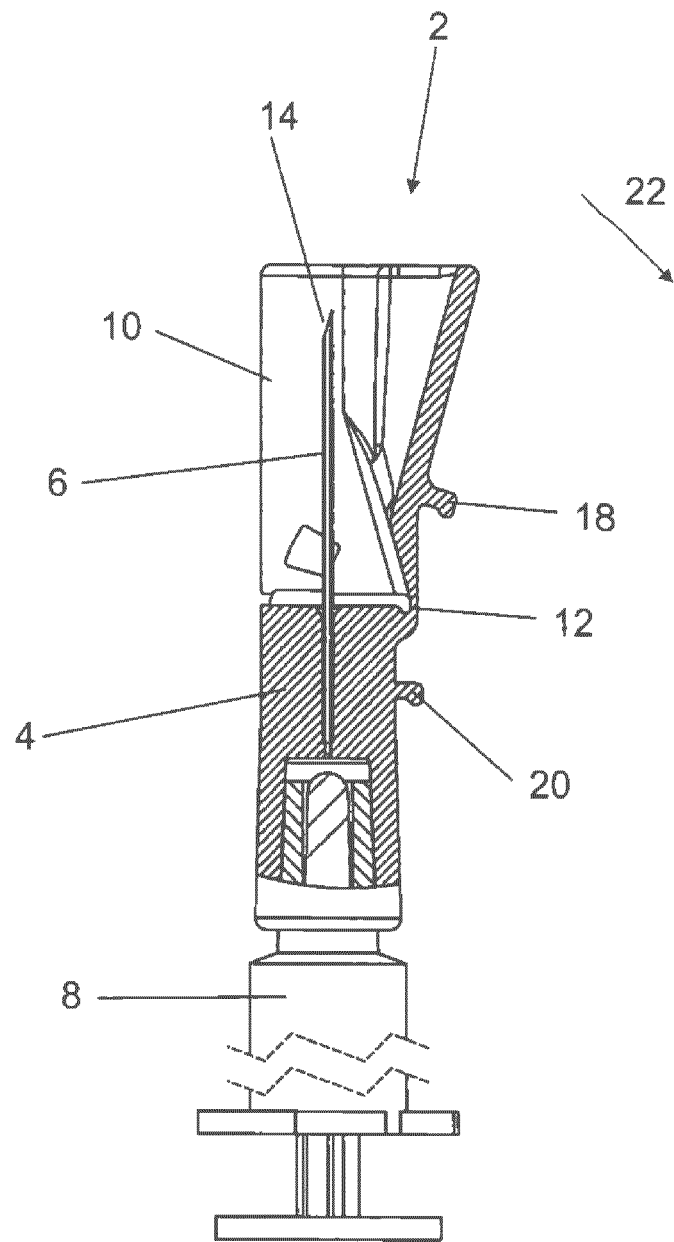
FIG. 4 shows a partially sectional side view of the cannula device 2 in the first position of the safety element 10.

To expose the cannula tip 14 for use of the cannula device 2, the safety element is pivoted about the hinge axis of the film hinge 12, out of the first position shown in FIG. 4 and in the direction of an arrow 22. In doing so, the user applies enough force, so that the fixation elements 16, 16' are detached, facilitated by the weakening of the material provided on them, so that the opposite ends of the safety element 10 and of the base body 4 are separated from one another, and the safety element 10 can be pivoted further clockwise until reaching the second position.

Figure 5:
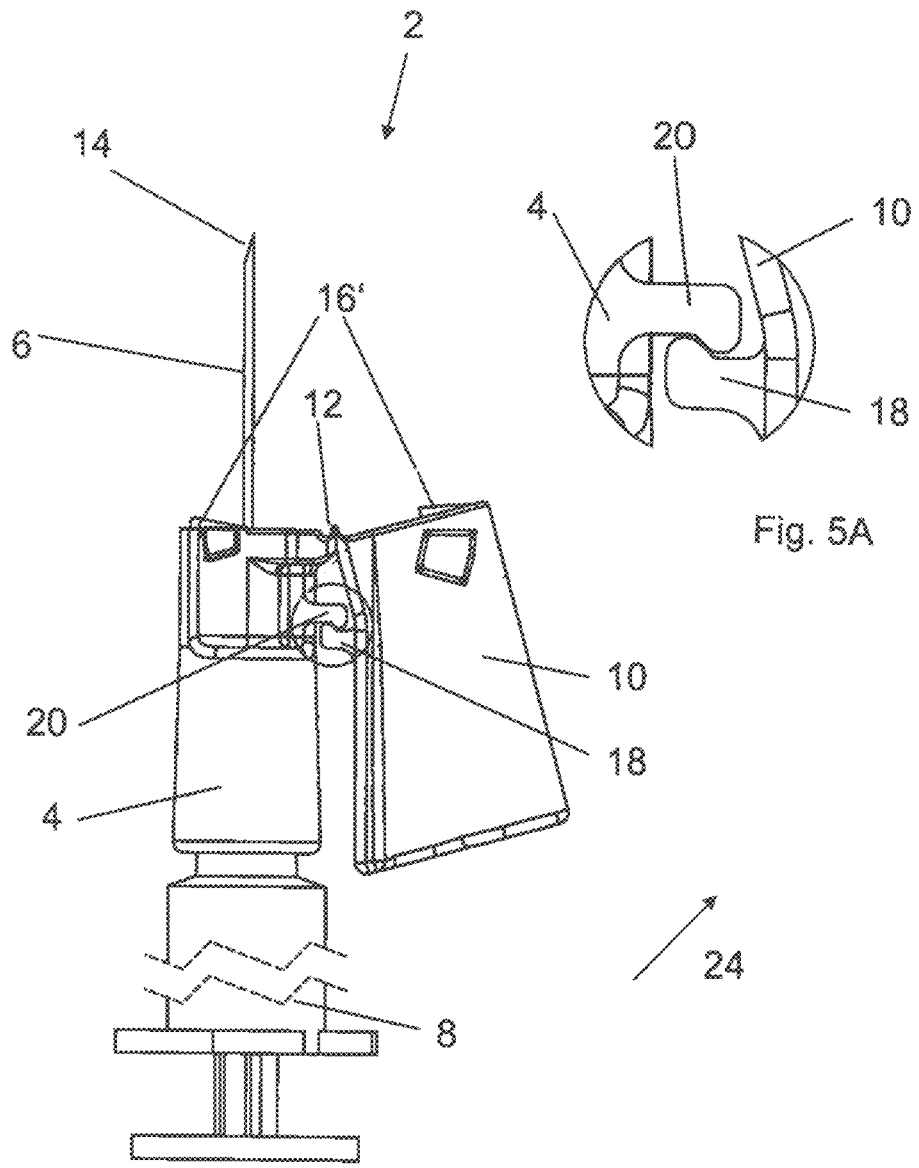

FIG. 5 shows the cannula device in the second position of the safety element 10, in which the cannula tip 14 of the cannula 6 is exposed for use of the cannula device. To prevent the safety element from unintentionally pivoting back into the first position and thereby interfering with use of the cannula device 2, the catch projections 18, 20 are locked to one another in the second position, as shown in FIG. 5 and as more clearly discernible in FIG. 5A, which is an enlarged detail from FIG. 5 in the area of the catch projections. As FIG. 5 also shows, the safety element 10 in the second position is pivoted by approx. 180° about the hinge axis of the film hinge 14 [sic; 12?] relative to the first position.

As FIG. 5 also shows, the fixation element 16' is detached, so that on both sides of the dividing line, i.e., on the safety element 10 and/or on the base body 4, residues of the fixation element 16' may remain, constituting an essentially triangular web part in each case in this exemplary embodiment.

Figure 6:
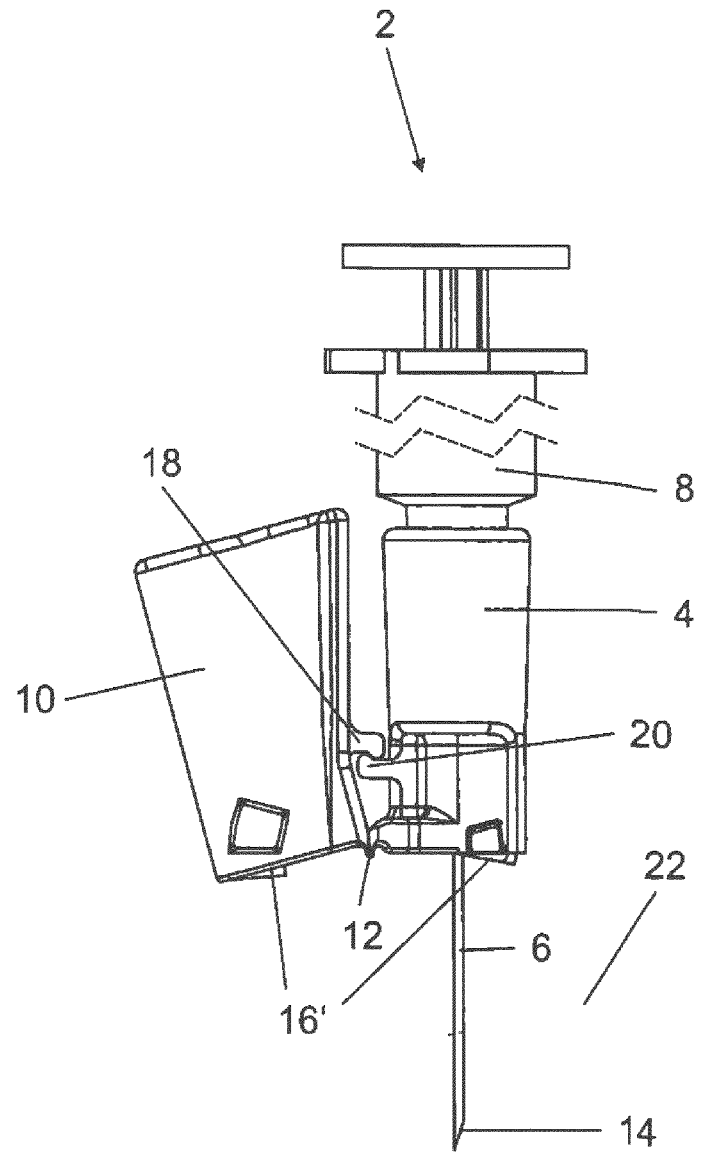

In the second position of the safety element, the cannula device 2 may be used and a puncture may be performed by means of the cannula 6, as indicated in FIG. 6, e.g., an injection of a liquid into human or animal tissue 22.

After using the cannula device 5, the safety element 10 in FIG. 5 may be pivoted in the direction of an arrow 24 in FIG. 5 counterclockwise back in the direction of the first position, where first the second fixation means formed by the catch projections 18, 20 are disengaged, namely with elastic deformation of the catch projections 18, 20.

Figures 7, 7A:
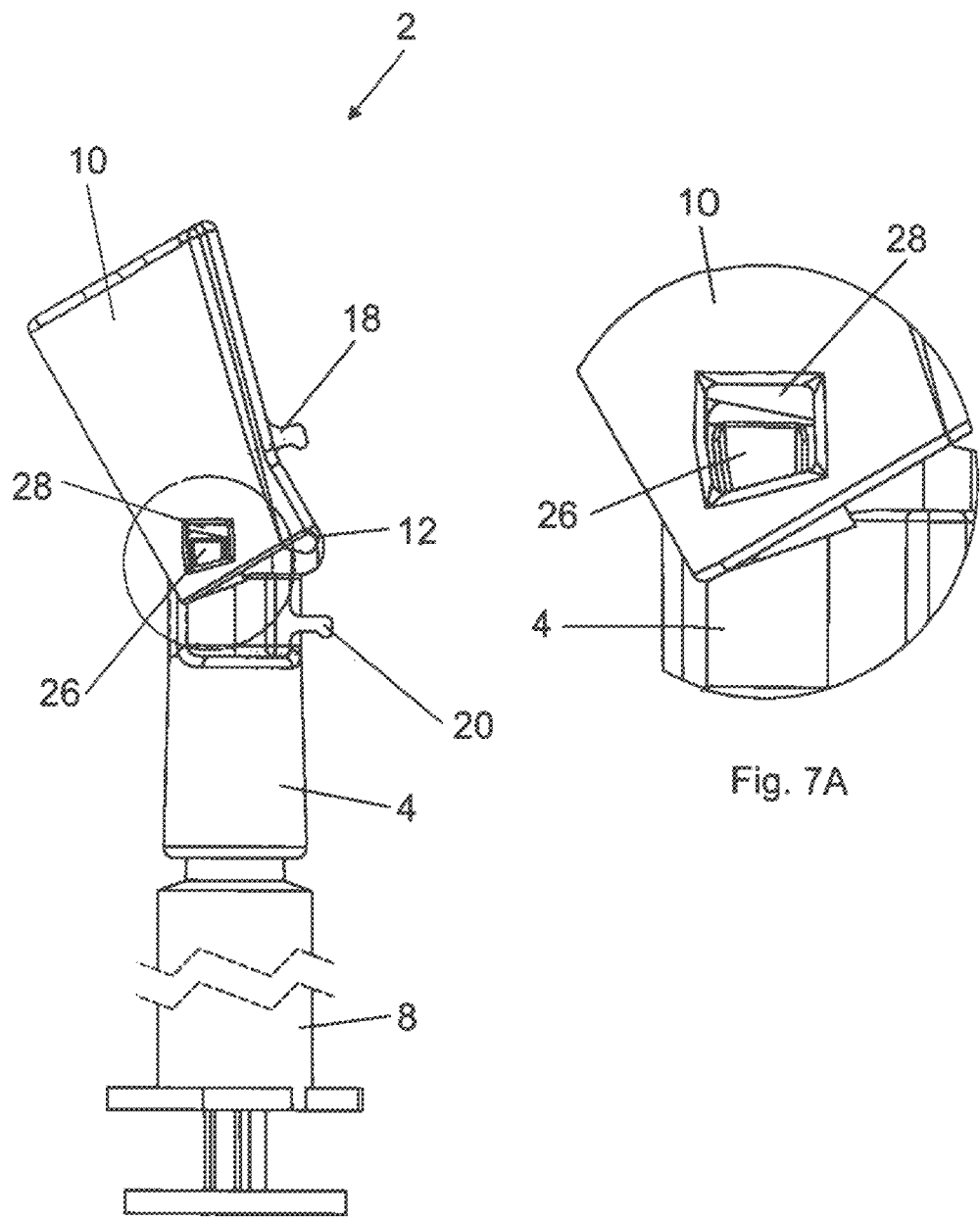

Following that, the safety element 10 is pivoted beyond the first position into a third position as shown in FIG. 7, which in turn corresponds to a safety position in which the cannula tip 14 is covered to protect the user from injury.

For fixation of the safety element 10 in this third position, third fixation means are provided, having a catch projection 26 (hereinafter also referred to as the first catch projection) arranged on the free axial end of the base body 4 and protruding in the radial direction of the base body 4, engaging in the third position in a window-like catch recess 28 (hereinafter also referred to as the first catch recess or catch receptacle) formed in the area of the free axial end of the safety element 10 facing the base body 4. The locking engagement between the catch projection 26 and the catch recess 28 is selected so that a permanent fixation of the safety element 10 in this position is achieved and an inadvertent disengagement, in particular without the use of a tool, is prevented. This prevents a user from inadvertently moving the safety element 10 back into a position in which the cannula tip 14 is exposed.

After the end of the use of the cannula device 2 and movement of the safety element 10 into the third position shown in FIG. 7, the cannula device 2 may be discarded together with or separately from the syringe 8.

Figure 8:
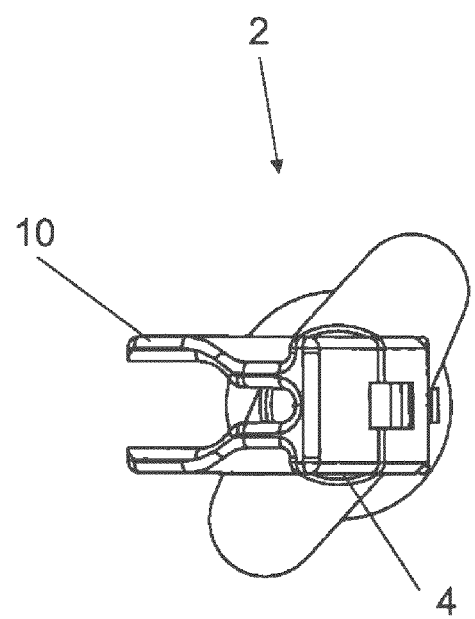

FIG. 7A shows a detail from FIG. 7 in the area of the catch projection 26 and the catch recess 28. FIG. 8 shows a view from above of the cannula device 2 in the third position of the safety element 10 according to FIG. 7.

Figure 9:
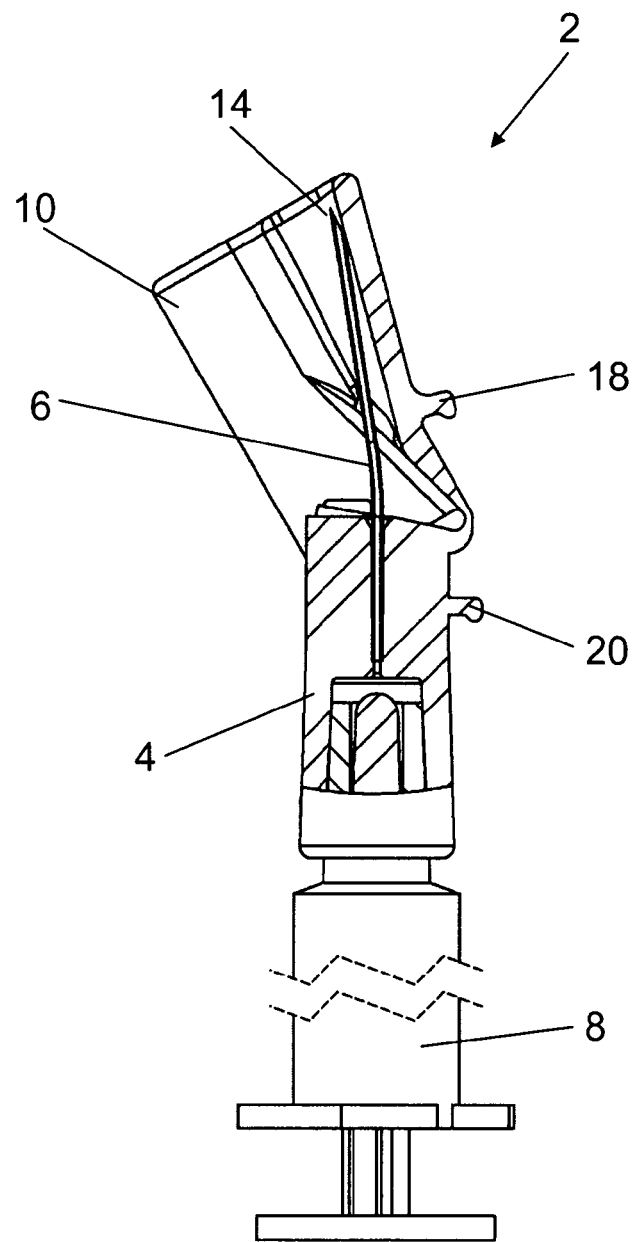

FIG. 9 shows a partially sectional side view of the cannula device 2 in the third position of the safety element 10, where it can be seen that the cannula tip 14 of the cannula 6 can be bent slightly in this third position.

FIGS. 10 through 16 show another embodiment of a cannula device and/or a cannula safety device 510, consisting of a base body 514, through which a cannula 512 passes, and showing a pivotable safety body 516, i.e., safety element or safety cap, which is preferably designed as an integral part with the base body and covers the cannula 512 in the as-delivered state (first position) as well as in a disposal position, which forms the third position. In the third position, the safety body 516 is locked to the base body 514 in such a way that unintentional detachment and thus renewed pivoting are no longer possible. Furthermore, it is possible that in the use position (second position), the cannula safety device 510 remains in a pivoted position, so that there cannot be any interference in the use of the cannula 512. In addition, the position of the cannula safety device 510 in the as-delivered state (first position) should differ from the disposal position (third position).

The safety body 516 with a U-shaped geometry is explained below. Other geometries such as a C-shaped cross section are also covered by the invention. Furthermore, the cannula 512 may be surrounded, e.g., sheathed directly by the base body 514 or connected to a conventional cannula attachment.

The base body 514 comprises a proximal section 518 and a distal section 520. The proximal section 518 directly surrounds the cannula 512. However, it does not go beyond the invention if the base body 514 is placed on a cannula attachment and locked to it, for example. The base body 518 [sic; 514?] is designed in particular as a Luer connector to allow a connection to a syringe body or to a tube, for example.

The distal section 520 comprises a web-shaped section 522 through which the cannula 512 passes and which develops into a section 524, which runs perpendicular to the former and protrudes laterally from the web-shaped section 522, so that this yields essentially a T-shaped geometry in which the web-like section 522 is the longitudinal leg and the section 524 running across the latter is the transverse leg.

The safety cap 516 in this exemplary embodiment is designed as a hollow cube having side walls 526, 528 and a rear wall 530 connecting the two. On the front side, the safety cap 516 is open to receive the cannula 512 into the cavity formed by the side walls 526, 528 and the rear wall 530 in the as-delivered state (first position, FIG. 11) as well as in the disposal position (third position, FIG. 13). Furthermore, in the exemplary embodiment, the safety cap 516 is closed at the head by a head wall 532. However, this is not an obligatory feature anymore than is the hollow cube shape of the safety cap 516, which also may also be designed to be a hollow cylinder, at least in some sections, for example.

The safety cap 516 is connected to the base body 514 by joints such as film hinges 534, 536. The film hinges 534, 536 proceed from sections 538, 540, which in turn protrude laterally from the web-shaped section and/or longitudinal leg 522 of the distal section 520 and are the side legs of a U-shaped section. Consequently, a clearance runs between the sections 538, 540, which form the side legs of the U shape and from whose outer edges the film hinges 534, 536 lead away. This clearance has a hinge joint 546 passing through it, extending in a cutout 548 of the rear wall 530 and thus leading away from the lower transverse edge area 550 of the rear wall 530 as well as from a section running perpendicular to and away from the web 522, connecting the side legs, i.e., sections 538, 540, from which the film hinges 534, 536 extend.

Figure 10:
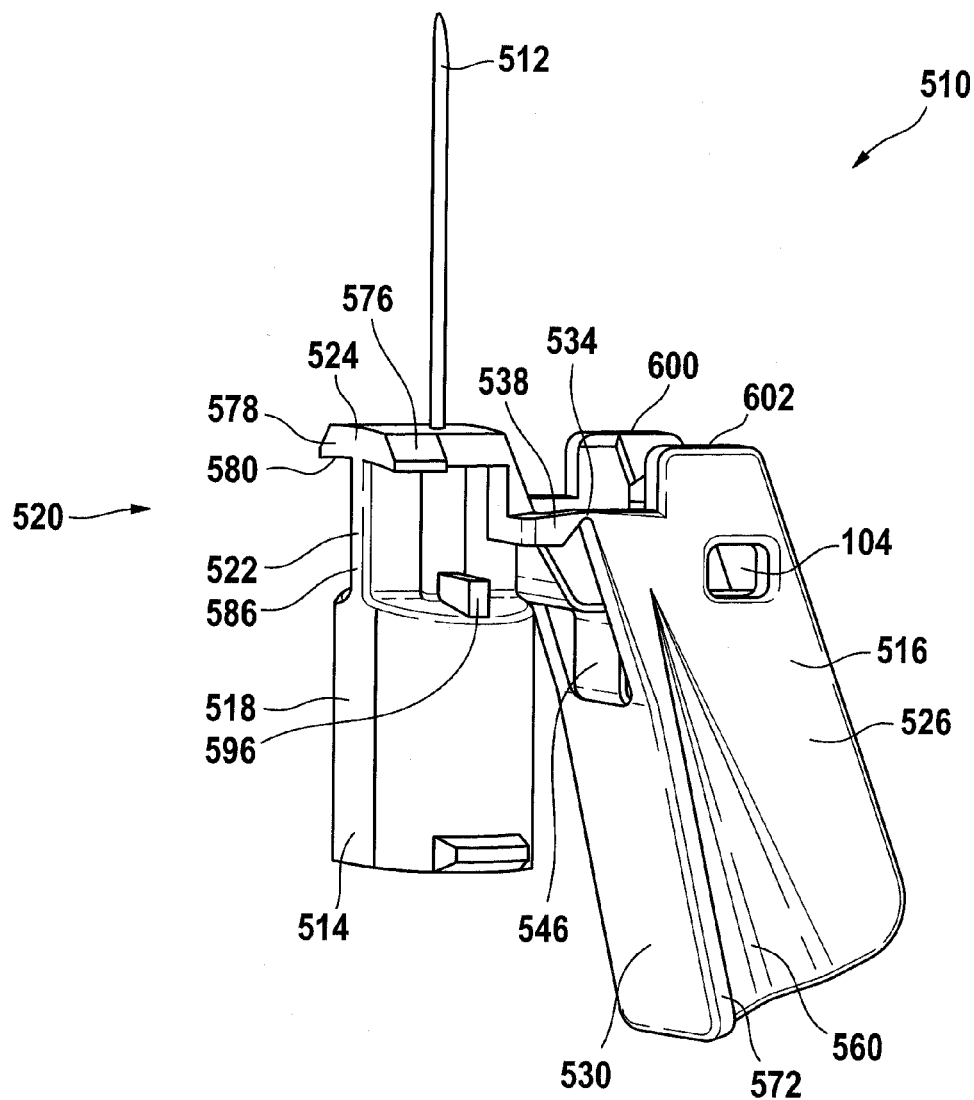

The hinge joint 546 is designed in one piece with the safety cap 516 and the base body 514, e.g., by an injection molding process. The hinge joint 546 has outer sections 549, 551 which develop into the transverse edge area 550 of the rear wall 530 and/or the transverse leg 542 of the distal section 522, between which there runs a flexible section 552 by means of which the hinge joint 546 is then held in a dead center position when the safety cap 516 is pivoted, when the safety cap is in a position pivoted away from the cannula 512, namely in the use position (second position) (FIG. 10). The hinge 546 then acts more or less like a folding hinge, such that it is adjusted by the relative movement between the articulation points on the distal section 520 of the base body 514 and the safety cap 516, such that in the useful state, a force acts on the safety cap 516 via the hinge 546, retaining the safety cap 516 in the open position. To achieve this, the film hinges 534, 536 and the articulation area of the hinge joint 546 must also run in planes that are offset relative to one another but are parallel to one another in the distal section 520 of the base body 514.

The diagram in the figure also shows that the side walls 526, 528 border V-shaped pockets 560, 562, starting from the head wall 532 and offering a problem-free grip of the safety cap 516 to pivot it. To form the pockets 560, 562, the side walls 526, 528 which run parallel to one another in sections 564, 566 on the open side, run toward the sections 564, 566 on the open side, so they are offset toward the inside in their rear sections 568, 570. The rear wall 530 also develops into wing-like edge sections 572, 574 which are extensions of the rear wall 530.

As shown in FIG. 10 in particular, the transverse leg 524 of the distal section 520 of the base body 514 is designed with a trapezoidal shape in its area running opposite the articulation area of the safety cap 516 with respect to the cannula 512, wherein each area running at one side of the longitudinal leg 522 forms a first catch projection 576, 578. The larger base 580 of the trapezoid formed in this way is facing the proximal area or section 518 of the base body 514 and may optionally have a curved concave shape with respect thereto, as shown in FIG. 10 in particular.

Beneath the section 524 forming the transverse leg of the trapezoid and away from the head area 592, 594 of the proximal section 518 of the base body 514, said head area runs in the form of a plateau, projections 596, 598 extend in the longitudinal direction of the cannula 512, these projections then forming stops for the lower transverse edges 600, 602 of the side walls 526, 528 of the safety cap 516 when the safety cap 516 is locked in the disposal position (FIG. 13), which is also referred to as the third position. First catch recesses 604, 606 in which the first catch projections 576, 578 engage like a hook in the disposal position (third position) are allocated to the first catch projection 576, 578.

Figure 12:
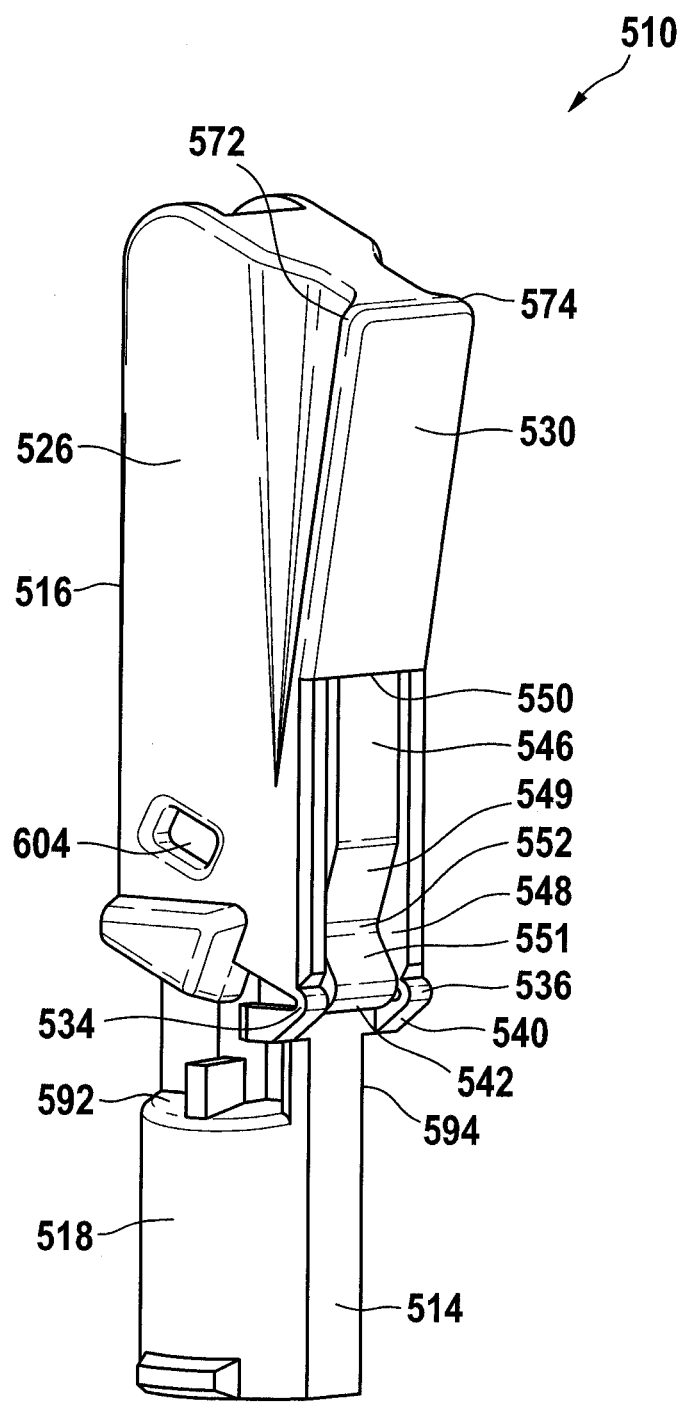

According to FIG. 12, the safety body 516 is affixed in the first position, i.e., in the as-delivered state relative to the base body 514, by a tamper-proof closure, which makes it possible to check visually and physically on whether the safety body 516 has been pivoted toward the base body 514, so that repeated use is not allowed.

Figure 11:
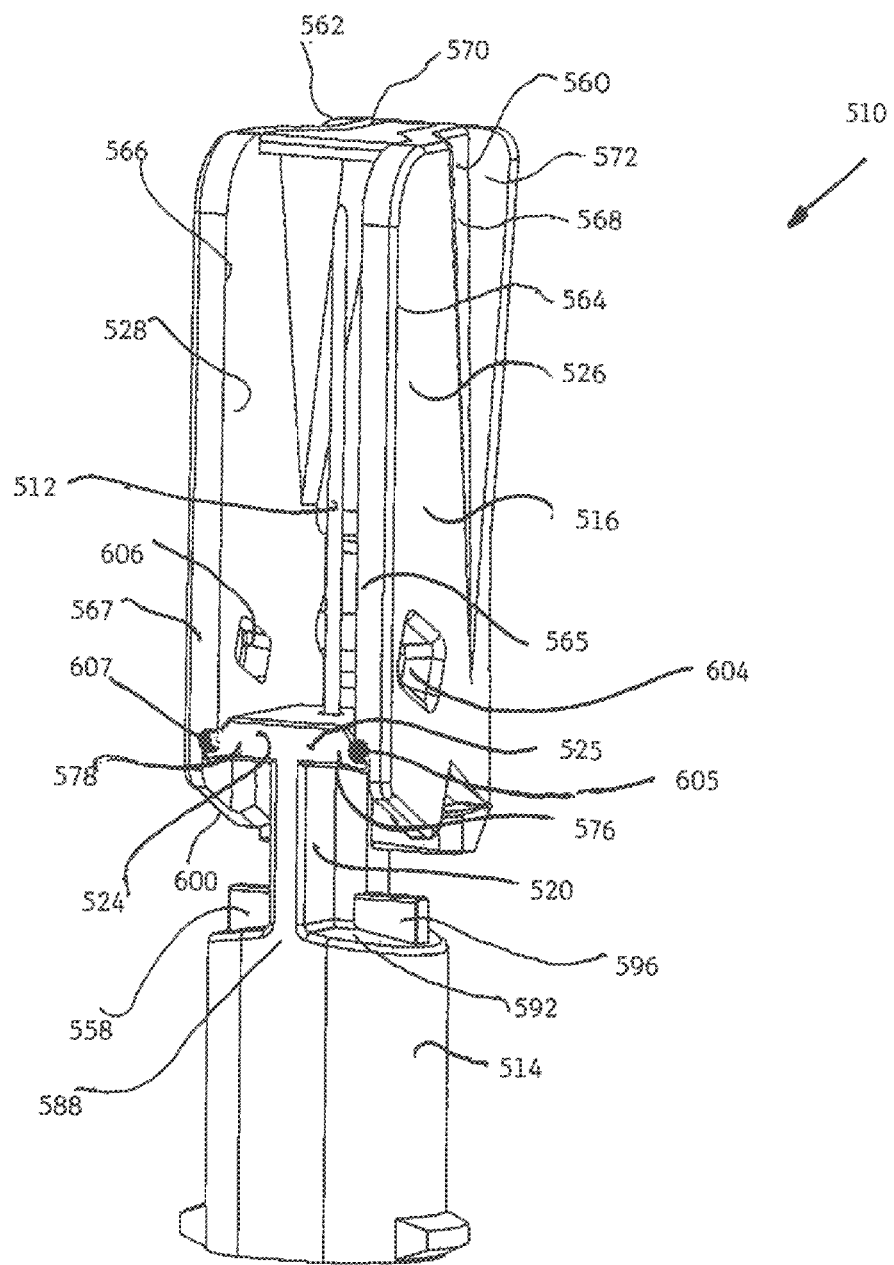

In the exemplary embodiment according to FIG. 11, this connection which forms a tamper-proof seal and is also referred to simply as a seal, is implemented by bonding the side walls 526, 528 of the safety body 516 to the transverse leg 524 of the distal section 520 of the base body 514, namely in the area of the end faces 565, 567 of the side walls 526, 528 and the end face 525 of the transverse leg 524. FIG. 12 also illustrates that the bonding takes place directly in the area of the ends of the transverse leg forming the first catch projections 576, 578. Regardless of this, a film membrane, which is produced by injection molding and can be detached, may additionally be provided between the base body 514 and the safety body 516, as explained in discussing the first exemplary embodiment according to FIGS. 1 through 9. The same thing is also true of the additional embodiments.

The connections formed by hot bonding in particular, and symbolized by the solid circles 605, 607, consequently ensure that the safety body 516 can be pivoted only when the connections 605, 607 are destroyed. To do so, a resistance must be overcome, so that a physical check on whether the cannula 512 has already been used and/or has been exposed may be performed. A visual check is likewise possible, because the connections 605, 607 are destroyed by the pivoting of the safety body.

Since the bonding (connections 605, 607) runs at a distance from the hinges 534, 536, this also ensures that a targeted force must act on the safety body 516 to destroy the bonded connections.

Other embodiments for a corresponding tamper-proof closure are of course likewise possible. For example, the safety body 516 may be attached to the base body 514 in the area of the transverse leg 524, e.g., by ultrasonic spot welding. There is also the possibility of providing other connections, such as adhesive bonds which must be formed in such a way that a targeted separation of the safety body 516 and the base body 514 is possible without damage to function parts.

Figure 14:
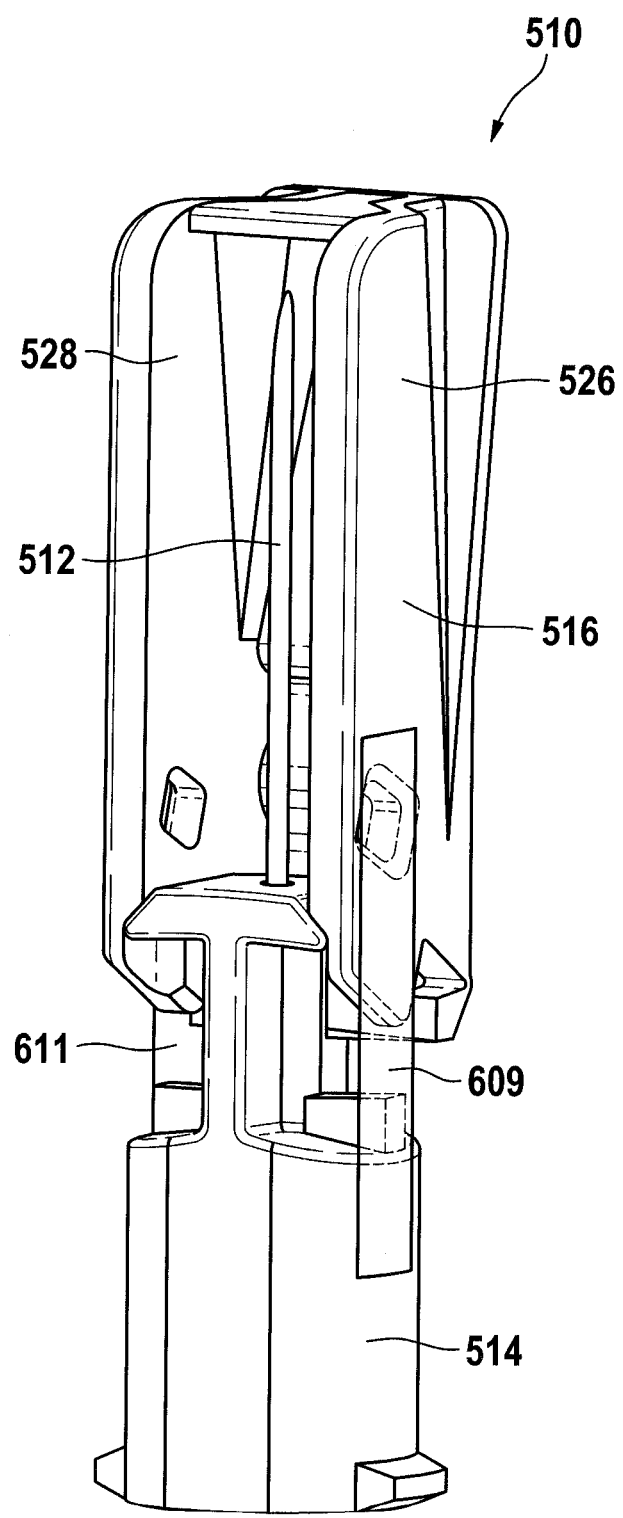

Another embodiment of a tamper-proof closure to be emphasized is shown in FIG. 14, where the safety body 516 is attached to the base body 514 by a strip of adhesive tape 609, 611, such as a label. In this diagram, the safety body 516 is in the first position, i.e., in the as-delivered state of the cannula 512. A visual as well as a physical check on whether or not the safety body 516 has already been pivoted toward the cannula 512 is also possible through the strip of adhesive tape and/or the label 609, 611. Preferably a corresponding strip of adhesive tape 609, 611, which should run in the axial direction of the cannula 512, extends along each exterior surface of the side walls 526, 528 of the safety body 516. To rule out the possibility of targeted release and reattachment of the strip of adhesive tape 609, 611, it should have predefined perforations, which do not allow renewed attachment.

In addition, a perforation (not shown) should also be provided in the strip of adhesive tape 609, 611 in the intermediate space between the base body 514 and the safety body 516 to avoid unnecessarily interfering with the pivoting of the safety body 516 when the cannula 512 is to be used.

If the cannula 512 is to be used, then the safety body 516 is pivoted clockwise about the film hinges 534, 536 in the diagrams, namely into the useful position (second position) (FIG. 10), in which the safety body 516 is held by means of the hinge joint 546. At the same time, the tamper-proof closure in the form of the hot bonding in FIG. 11 and/or the label and/or strip of adhesive tape 609, 611 according to FIG. 14 is destroyed. In the useful position (second position), the cannula 512 is freely accessible and consequently can be punctured. After using the cannula 512, the safety body 516 is pivoted in the direction of the cannula 512 (therefore, counterclockwise in the diagrams) to such an extent that the first catch projections 576, 578 engage in the catch recesses 604, 606. The pivoting is additionally limited by the fact that the lower transverse edges 600, 602 of the side walls 526, 528 come to a stop against the stops 596, 598.

Because of the cross-sectional geometry of the catch projections 576, 578, the catch recesses 604, 606 likewise have a rectangular geometry in the plane of the side walls 526, 528.

Figure 13:
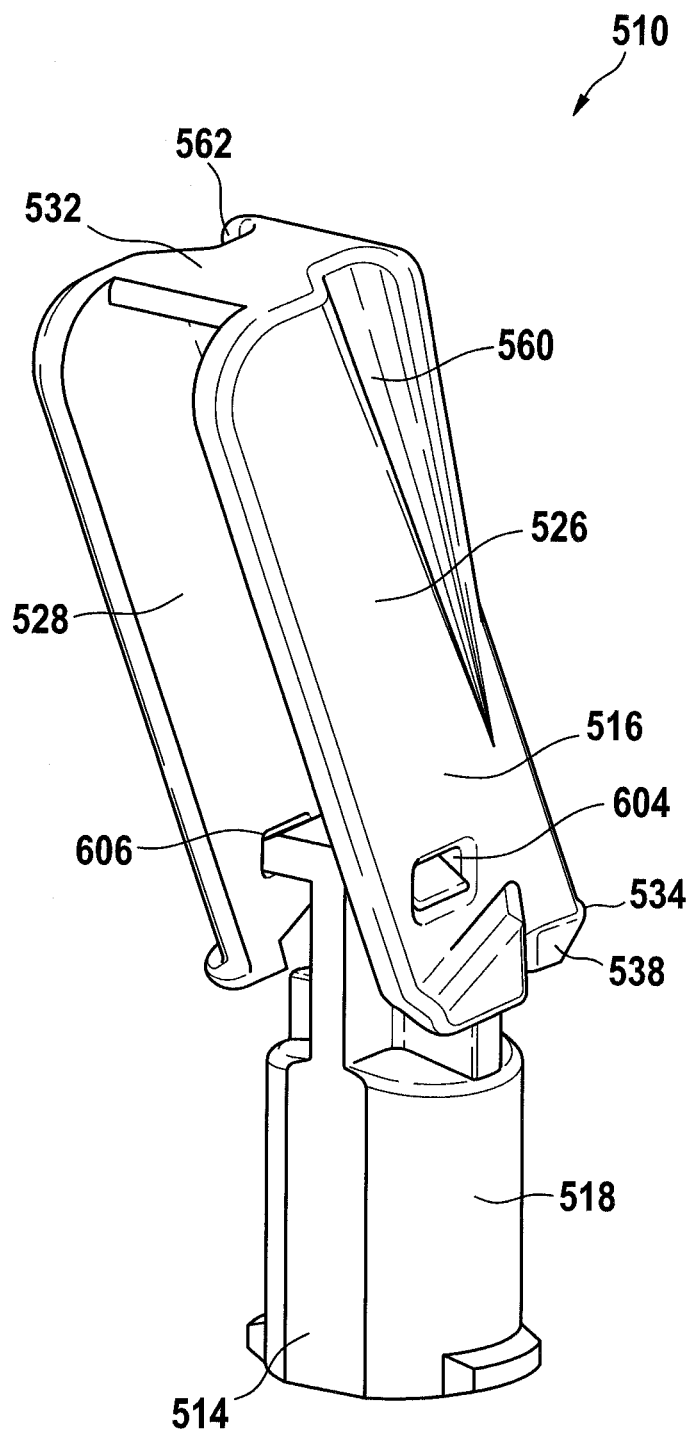

As shown in FIG. 13 in particular, the respective lower side of the first catch projections 576, 578 rests on the lower edge of the first catch recesses 604, 606, so that pivoting is interrupted when a force acts on the safety body 516. In addition, the catch projections 576, 578 should be positioned with respect to the catch recesses 604, 606 relative to the hinge joints 534, 536, so that when the catch projections 576, 578 engage in the catch recesses 604, 606, the cannula 512 is bent. In this way, if, contrary to expectation, an attempt is made to pivot the safety body 516 out of the disposal position (third position), it will be obvious visually that the cannula 512 has already been used.

In the exemplary embodiment, the base body 514 directly surrounds the cannula 512. A connection may be established here by adhesive bonding or by injection molding. However, it does not depart from the inventive teaching if the inventive cannula safety device is distributed independently of the cannula, to then be pushed onto the attachment of the cannula, for example, or to be attached to a syringe body, e.g., a prefilled syringe, from which a cannula in turn protrudes.

Figure 15:
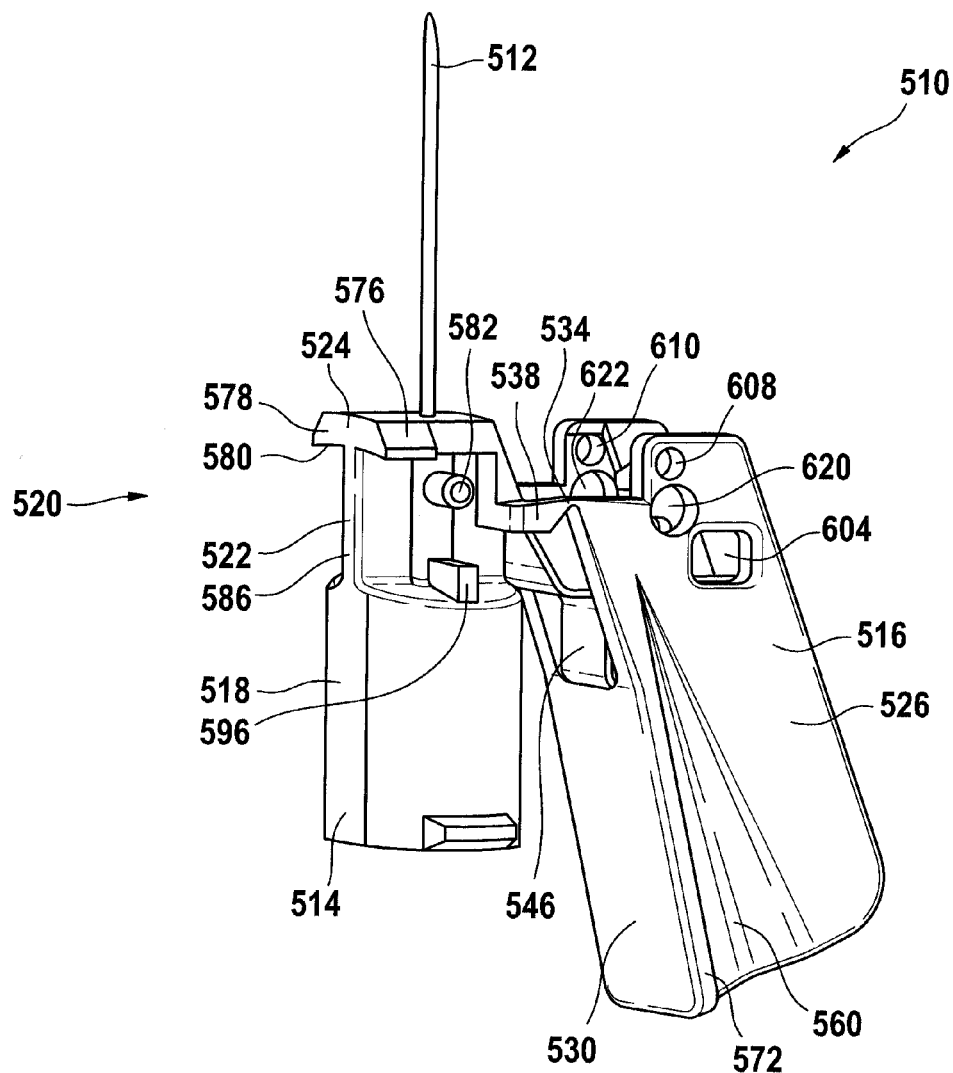

On the basis of FIG. 15, it shall now be explained how the safety body 516 may be connected to the base body 514 not only by means of a tamper-proof closure, as is shown in principle in FIGS. 2, 11, 14, but additionally by a locking engagement in the as-delivered state (first position).

The second catch projections 582, 584 may thus protrude laterally away from the longitudinal leg 522, running symmetrically with the plane spanned by the longitudinal leg 522 and having a cylindrical shape. The second catch projections 582 run approximately in the middle area between the longitudinal edges 586, 588 of the web-like section 522, i.e., the longitudinal leg of the distal section 520 of the base body 514 having a T-shaped geometry, and beneath the first catch projections 576, 578.

The first and second catch recesses 604, 606 and/or 608, 610 are allocated to the first and second catch projections 576, 578 and/or 582, such that the second catch projections 582 engage in the second catch recesses 608, 610 when the cannula safety device 510 is in the as-delivered state, i.e., in the first position.

In order for the second catch projections 582 not to be able to press the side walls 526, 528 outward in the disposal position (third position), third recesses 620, 622 are provided in the side walls 526, 528, with the second catch projections 582 engaging in these recesses when in the disposal position.

Based on the cross-sectional geometry of the projections 576, 578, the first catch recesses 604, 606 likewise have a rectangular geometry in the plane of the side walls 526, 528. On the other hand, the catch recesses 608, 610, 620, 622 have a circular cross section, such that the third recesses 620, 622 have a larger cross section than the second recesses 608, 610. In particular the second catch recesses 608, 610 are adapted to the cross-sectional geometry of the second catch projections 582, such that there is a relatively minor play.

Figure 16:
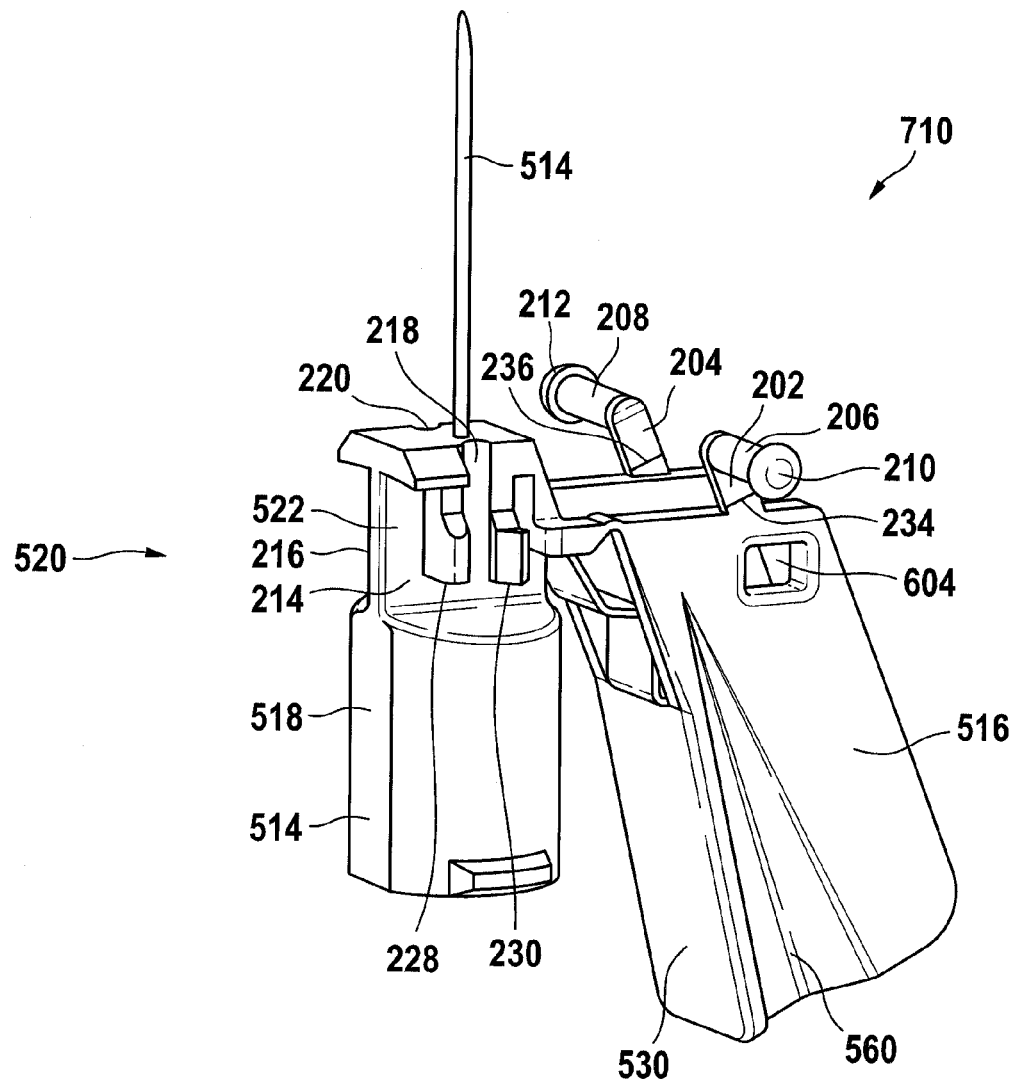
Figure 17:
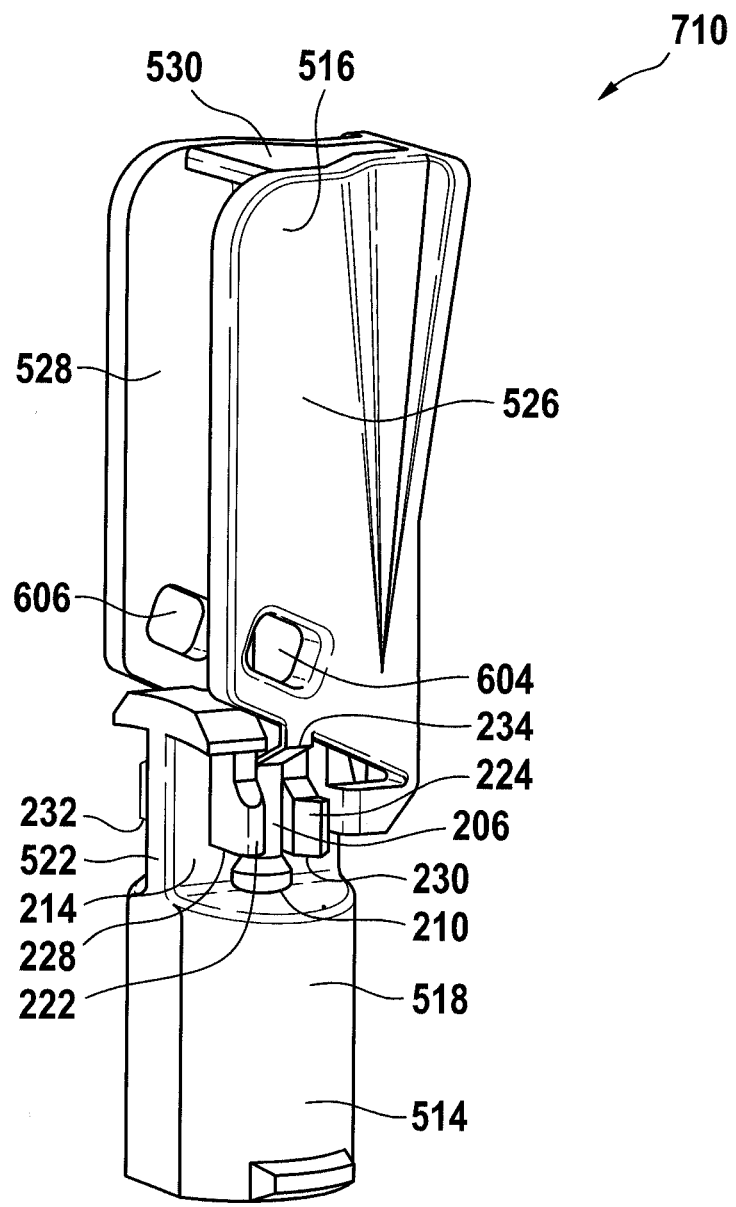
Figure 18:
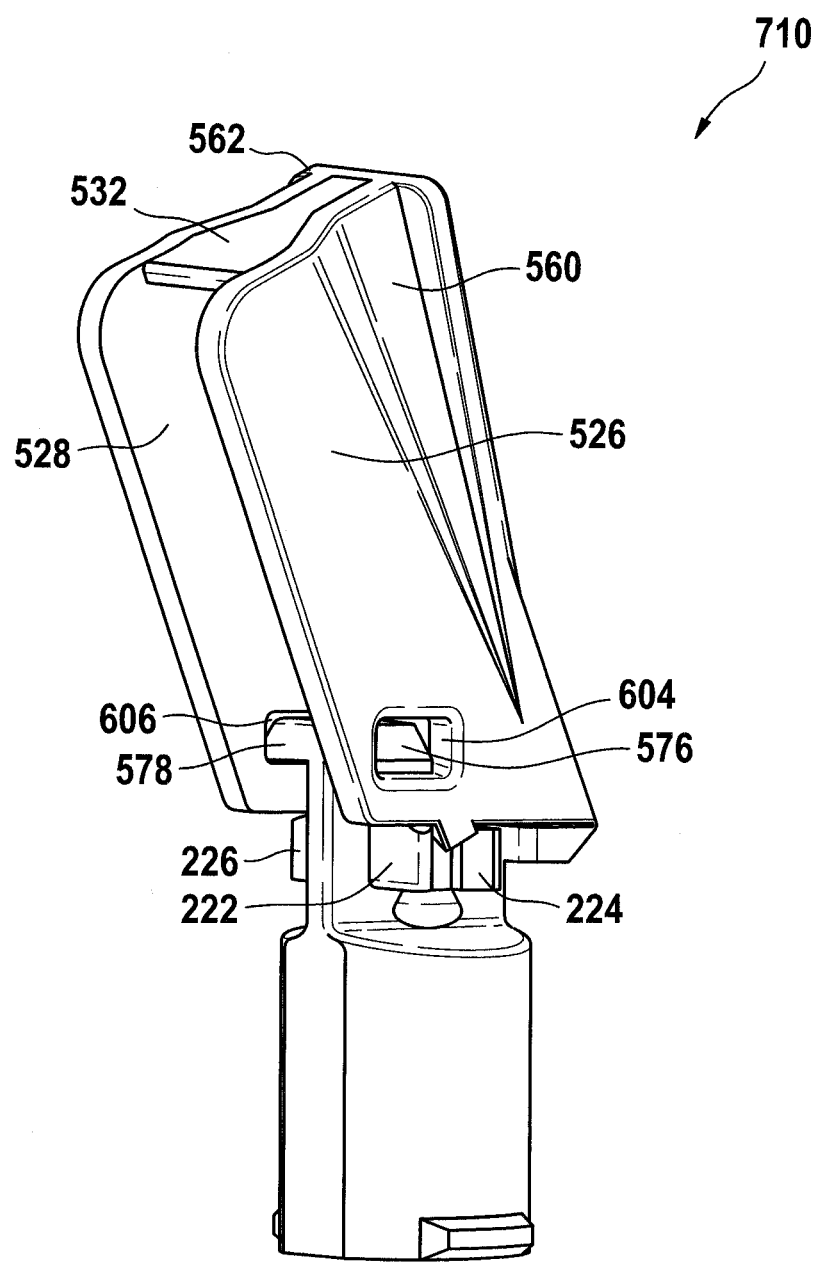

FIGS. 16 to 18 show another embodiment of a cannula safety device 200, in which essentially the same reference numerals are used for elements corresponding to those in the exemplary embodiment of the cannula safety device 510 according to FIGS. 10 to 15.

Consequently, the cannula safety device 710 likewise consists of the base body 514 and the safety body 516, which corresponds to the exemplary embodiment of FIGS. 10 to 15 with respect to the hinge connection to the base body 514, the design of the safety body 516 and of the first catch projections 576, 578 and the first catch recesses 604, 606. The same thing is also true with regard to the hinge joint 546 by means of which the safety body 516 is held in the useful state in a dead center position.

As the drawing shows, in the as-delivered state (first position), the safety body 516 is not affixed by means of second catch projections, which engage in second catch recesses of the safety body 516, but instead the design described below is selected. Regardless thereof, a tamper-proof closure should be provided, no matter if fixation by means of the second catch projections (FIG. 15) or the design described below is inventive.

Flat web-shaped sections 202, 204 thus protrude from the lower transverse edge area 600, 602 of the side walls 526, 528, such that after injection molding (assembly position, FIG. 16), these web-shaped sections run in the plane spanned by the side walls 526, 528. Cylindrical projections 206, 208 that protrude away from the web-like sections 202, 204 have toroidal reinforcements 210, 212 on their free ends.

Webs 222, 224, 226 extend away from the longitudinal leg, i.e., the web-type section 522 of the distal section 520 of the base body 514, bordering a channel 218, 220 on each side 214, 216, the spacing of these webs being adapted to the diameter of the cylindrical projections 206, 208, such that in the as-delivered state (first position, FIG. 17), the projections 206, 208 are engaged and come to lie with their toroidal ends 210, 212 beneath the lower edges 228, 230, 232 of the web-type projections 222, 224, 226. The web running parallel to the web 226 and bordering the channel 220 is not visible in these figures.

If the cannula 512 is to be used, i.e., exposed, then the safety body 516 is pivoted clockwise in the exemplary embodiment. Then the cylindrical projections 206, 208, which are securely clamped in the channels 218, 220 between the webs 222, 224, 226, are separated from the flat web-type sections 202, 204, i.e., they are torn away. To facilitate this, predetermined breaking points 234, 236 are formed in the web-type sections 202, 204. Since the cylindrical projections 206, 208 are securely clamped between the web-type projections 222, 224, 226, these remain in the channels 218, 220, which subsequently form recesses for the cylindrical projections 206, 208.

After use of the cannula 512, the safety body 516 is pivoted clockwise in the direction of the cannula 512 to such an extent that the first catch projections 576, 578 engage in the first catch recesses 604, 606 in the side walls 526, 528.

After use of the cannula 512, the safety cap 516 is pivoted clockwise in the direction of the cannula 512 to such an extent that the first catch projections 576, 578 engage in the first catch recesses 604, 606 in the side walls 526, 528.

If the projections 596, 598 leading away from the plateau-type head surfaces 592, 594 of the base body 514 in the cannula safety device 510 of FIGS. 10 to 15 serve as stops for the proximal transverse edges 600, 602 of the side walls 526, 528, then with the cannula safety device 710, the upper edges of the webs 228, 230, 232 bordering the channels 218, 220 execute the same function.

Regardless of this, the base body 514 of the safety device 710 has the same design as the cannula safety device 510.

Figure 19:
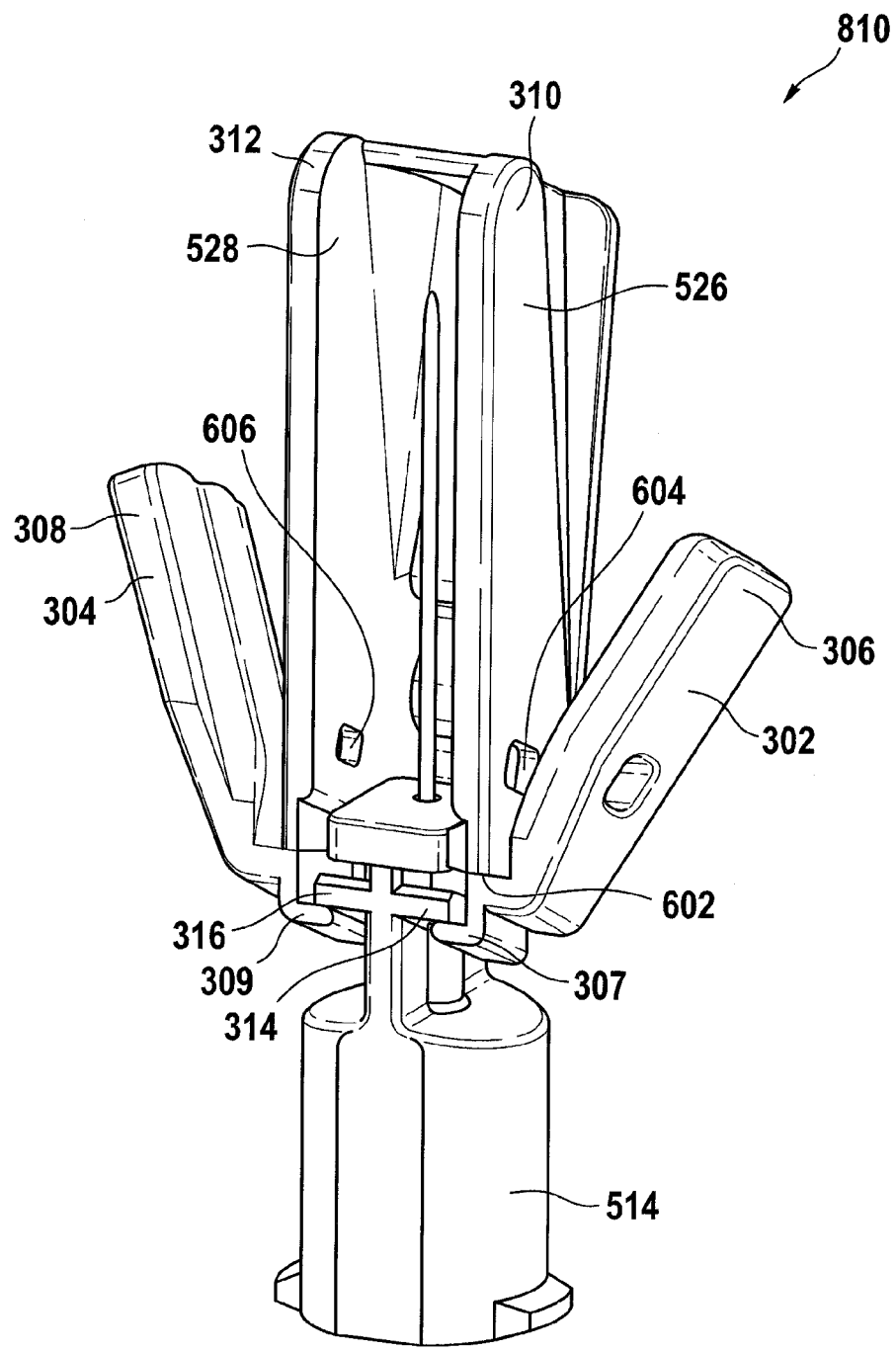

FIG. 19 shows another embodiment of a cannula safety device 810, which implements the same structural features as already explained above on the basis of the exemplary embodiments of FIGS. 1 to 18 with respect to the connection of the base body 514 to the safety body 516, the film hinges 534, 536, the hinge joint 546 and the locking engagement of the safety body 516 after the use of the cannula 512, i.e., in the disposal state (third position).

In deviation from this, however, the following construction is selected for locking engagement of the safety body 516 in the as-delivered state.

Pivotable two-armed legs or wings 302, 304 lead away from the lower transverse edge area 600, 602 of the side walls 526, 528 and extend with the first arms or sections 306, 308 along the exterior surfaces 310, 312 of the side walls 526, 528. The sections 307, 309 of the wings 302, 304 running beyond the transverse edges 600, 602 and/or articulation areas of the wings 302, 304 have L-shaped geometries which engage beneath web-type projections 314, 316 in the as-delivered state (FIG. 19), leading away from the web-type section 522, i.e., the longitudinal leg of the distal section 520 of the base body 514 having the T-shaped geometry. The web-type projections 314, 316 run symmetrically with the plane spanned by the longitudinal leg 522 and falling in the direction of the articulation area of the safety body 516. This should ensure that in the as-delivered state (FIG. 19), the inside surfaces of the L-shaped sections 307, 309 of the wings 302, 304 are in surface contact with the undersides of the catch projections 314, 316.

If the cannula 512 is to be exposed, i.e., the safety body 516 is to be pivoted clockwise in the exemplary embodiment shown here, then the wings 302, 304, i.e., their sections 306, 308 running along the side walls 526, 528 are pivoted in the direction thereof so that the sections 307, 309 become disengaged from the catch projections 314, 316 so that pivoting is possible, as illustrated in FIGS. 13 and 14.

Regardless of the features explained above, a tamper-proof closure can likewise be provided here. Again there is a locking engagement in the third position, as already explained in detail above.

If the cannula devices and/or safety devices 2, 510, 710, 810 have been explained on the basis of exemplary embodiments in which the base body 4, 514 directly surrounds the cannula 6, 512, i.e., is fixedly connected to it by adhesive bonding or injection molding, then of course this does not go beyond the scope of the inventive teaching if the inventive cannula safety device is distributed independently of the cannula, and is then pushed onto the attachment of a cannula or connected to a syringe body, e.g., a prefilled syringe from which a cannula in turn protrudes.

The invention claimed is:

1. A cannula device comprising:
a base body made of plastic, said base body comprising a cannula with a cannula tip;
said base body having a safety body, which is integral with the base body and hingedly connected thereto; wherein the safety body is configured to be moved in relation to the base body out of a first position, in which the cannula tip in an as-delivered state of the cannula device is covered to protect the user from injury, into a second position, in which the cannula tip is exposed for use of the cannula device, and wherein, after the use of the cannula device, the safety body is configured to be moved back into a third position in which the cannula tip is covered to protect the user from injury and the safety body is irreversibly locked onto the base body by a third fixation means, the third fixation means comprising
at least one first catch projection protruding away from the base body and at least one first catch recess allocated to the at least one catch projection in at least one side wall of the safety body; the safety body in the as-delivered state being connected to the base body by a tamper-proof closure;
wherein the base body has a proximal section comprising a Luer cone or a Luer connecting body, and wherein the base body has a distal section having a T-shaped geometry;
wherein, to form the tamper-proof closure, the distal section is bonded or ultrasonically welded to the safety body, or, leading away from at least one side of a longitudinal leg of the T-shaped distal section of the base body, a recess for a projection connected to the at least one side wall of the safety body, and pivotable along the side, is connected to the side wall via a breaking point, and the projection is affixed in the recess in the first position.

2. The cannula device according to claim 1, wherein the safety body is hinge-connected to the base body by two articulation points spaced a distance apart.

3. The cannula device according to claim 1, wherein the third fixation means affixes the safety body in the third position to secure the safety body against inadvertent detachment, without using a tool.

4. The cannula device according to claim 1, wherein the third fixation means is designed in one piece integral with at least one of the safety body and the base body.

5. The cannula device according to claim 1, wherein an inside surface of the rear wall of the safety body is positioned closer to the cannula in the disposal state than in the as-delivered state (first position), such that the cannula is bent by means of the safety body in the disposal state.

6. The cannula device according to claim 1, wherein the cannula passes through the longitudinal leg of the distal section.

7. The cannula device according to claim 1, wherein the projection, which is connected to the recess via the breaking point is locked in the recess.

8. The cannula device according to claim 1, wherein a recess for a projection connected to one of the at least one side wall via a breaking point leads away from each side of the longitudinal leg of the distal section.

9. The cannula device according to claim 1, wherein the projection has a cylindrical shape with a reinforcement present on its free end, engaging beneath the recess when positioned in the recess in a fixed manner.

10. The cannula device according to claim 1, wherein for positioning the safety body in the first position, the projection is pivotable about the predetermined breaking point.

11. The cannula device according to claim 1, wherein the tamper-proof closure runs at a distance from at least one articulation point, by means of which the safety body is connected to the base body.

12. The cannula device according to claim 1, wherein the safety body is bonded to the distal section of the base body.

13. The cannula device according to claim 1, wherein each side wall of the safety body is bonded to the nearby catch projection or is connected to it by ultrasonic spot welding.

14. The cannula device according to claim 1, wherein the connection forming the tamper-proof closure between the safety body and the base body is formed by the at least one side wall and the transverse leg of the distal section in the area of the end faces.

15. The cannula device according to claim 1, wherein the base body together with the safety body is designed as an injection-molded part made of plastic.

16. The cannula device according to claim 1, wherein the base body is designed to surround a cannula attachment.

17. The cannula device according to claim 1, wherein the base body is connected to the cannula attachment or by locking engagement.

18. The cannula device according to claim 1, wherein the cannula device is connected to a syringe body of a prefilled syringe.

19. The cannula device according to claim 1, wherein two second catch projections running symmetrically with a longitudinal leg protrude away from the longitudinal leg of the distal section of the base body, a second catch recess in the at least one side wall being allocated to every second catch projection.

20. The cannula device according to claim 19, wherein the second catch recess is an opening in the at least one side wall.

21. The cannula device according to claim 1, wherein a rear wall has sections protruding laterally beyond the at least one side wall to serve as handles.

22. The cannula device according to claim 21, wherein the at least one side wall have first sections running parallel to one another on an open side, developing into second sections, whose spacing, at least in the area remote from the joint, is reduced in the direction of the rear wall, and the second sections develop into third sections, which are bordered by the rear wall and/or extensions thereof.

23. The cannula device according to claim 1, wherein the projection is connected to the side wall via a pivotable web shaped section having the breaking point.

24. The cannula device according to claim 23, wherein the web-shaped section runs in the plane spanned by the at least one side wall from which the projection protrudes at a right angle, before the safety body is pivoted into and positioned in the first position.

25. The cannula device according to claim 1, wherein the recess is bordered by two webs running parallel to one another and preferably parallel to the cannula and protruding away from the longitudinal leg of the distal section of the base body.

26. The cannula device according to claim 25, wherein the webs border a channel, which forms the recess and is enlarged conically at one end.

27. The cannula device according to claim 1, wherein the safety body is affixed in the second position by a second fixation means.

28. The cannula device according to claim 27, wherein the second fixation means is designed in one piece with at least one of the safety body and the base body.

29. The cannula device according claim 27, wherein the second fixation means has a catch means.

30. The cannula device according to claim 1, wherein the safety body is connected to the base body by a dead center arrangement having a dead center in the second position of the safety body.

31. The cannula device according to claim 30, wherein the dead center arrangement is formed by the hinge connection between the safety body and the base body.

32. The cannula device according to claim 30, wherein a retaining hinge connecting the base body to the safety body is connected to the dead center position in the useful position of the cannula (second position) between the two articulation points and/or areas, which are spaced a distance apart from one another.

33. The cannula device according to claim 32, wherein the retaining hinge has two outer sections, connected first to the base body and secondly connected to the safety body and/or its rear wall and/or leading away from them, and consists of a flexible inner section running between them.

34. The cannula device according to claim 1, wherein the safety body is affixed in the first position by a first fixation means before use of the cannula device.

35. The cannula device according to claim 34, wherein the first fixation means has a catch means.

36. The cannula device according to claim 34, wherein the first fixation means has at least one fixation element, which is detached by moving the safety body out of the first position and into the second position.

37. The cannula device according to claim 36, wherein the fixation element is a film.

38. The cannula device according to claim 36, wherein the fixation element has at least one weakening in the material, such that detachment of the fixation element is facilitated when the safety body is moved out of the first position and into the second position.

39. The cannula device according to claim 36, wherein at its one end, the fixation element is designed in one piece with at least one of the base body and the safety body and at its other end, is connected to at least one of the safety body and to the base body by a connecting means.

40. The cannula device according to claim 1, wherein at least one second catch projection, to which is allocated a second catch recess in the at least one side wall of the safety body, protrudes away from a longitudinal leg of the distal section of the base body in the area of the cannula.

41. The cannula device according to claim 40, wherein in the first position of the safety body, the at least one second catch projection is engaged in the second catch recess.

42. The cannula device according to claim 40, wherein a third catch recess runs in the at least one side wall between the first and the second catch recesses, the second catch projection protruding into this third catch recess when the safety body is in the disposal position (third position).

43. The cannula device according to claim 42, wherein the second catch projection has a cylindrical shape.

44. The cannula device according to claim 42, wherein at least one of the second and third catch recesses has a circular geometry in the plane of the at least one side wall.

45. The cannula device according to claim 42, wherein the cross section of the third catch recess has a larger cross section than the second catch recess in the plane of the at least one side wall.

46. The cannula device according to claim 1, wherein two first catch projections running symmetrically with a plane lead away from the base body, and a first catch recess in the at least one side wall of the safety body is allocated to each catch projection, with the cannula running in the plane.

47. The cannula device according to claim 46, wherein the two first catch projections protrude away from a web-shaped section of the base body, which extends along the cannula and through which the cannula passes.

48. The cannula device according to claim 46, wherein the two first catch projections develop one into the other and have a trapezoidal geometry with a base leg, which is larger distally from the proximal area of the base body.

49. The cannula device according to claim 46, wherein with one of said catch projections locked in the first catch recess, said catch projection runs completely with its free outer longitudinal edges inside the first catch recess.

50. The cannula device according to claim 46, wherein sections of the transverse leg of the T-shaped distal section of the base body form the first catch projections.

51. The cannula device according to claim 46, wherein the first catch recess has a rectangular geometry in the plane of the at least one side wall, and openings are present in the at least one side wall.

52. The cannula device according to claim 46, wherein the first catch projections lead away from a first section of a transverse leg of the distal section of the base body, said first section running on one side of the cannula, and articulation points and/or articulation areas of the base body lead away from a second section of the transverse leg running on the opposite side of the cannula.

53. The cannula device according to claim 52, wherein the articulation points and/or articulation areas lead away from webs which protrude away from the longitudinal leg in the area of the second section of the transverse leg.

* * * * *